United States Patent [19]

Yasuda et al.

[11] Patent Number: 4,599,333
[45] Date of Patent: Jul. 8, 1986

[54] HYDRAZINOPYRIDAZINE COMPOUND, PROCESS FOR PRODUCTION THEREOF, AND USE THEREOF AS MEDICAMENT

[75] Inventors: Kikuo Yasuda, Yokohama; Takayuki Takezaki, Kawasaki; Rikio Ohuchi, Kawasaki; Hiroshi Ohuyabu, Kawasaki; Yoshitaka Tanimoto, Yokohama; Toshimi Seki, Kawasaki; Takashi Yamaguchi, Yokohama; Akihiro Izumi, Machida; Norio Himori; Tsutomu Ishimori, both of Kawasaki, all of Japan

[73] Assignee: Teikoku Hormone Mfg. Co., Ltd., Tokyo, Japan

[21] Appl. No.: 591,904

[22] Filed: Mar. 22, 1984

Related U.S. Application Data

[63] Continuation of Ser. No. 388,476, Jun. 14, 1982, abandoned.

[51] Int. Cl.[4] .................. C07D 237/20; C07D 237/22; A61K 31/50
[52] U.S. Cl. .................................. 514/247; 544/239
[58] Field of Search ................. 544/239, 241; 424/250

[56] References Cited

U.S. PATENT DOCUMENTS

| | | | |
|---|---|---|---|
| 3,514,465 | 5/1970 | Posselt et al. ...................... | 546/328 |
| 3,723,524 | 3/1973 | Augstein et al. .................... | 424/250 |
| 3,891,641 | 6/1975 | Pifferi ................................ | 424/250 |
| 4,027,027 | 5/1977 | Jaeggi et al. ....................... | 424/266 |
| 4,115,575 | 9/1978 | Frei et al. .......................... | 424/250 |
| 4,324,788 | 4/1982 | Dorigotti et al. ................... | 544/239 |

FOREIGN PATENT DOCUMENTS

| | | | |
|---|---|---|---|
| 959845 | 12/1974 | Canada ............................. | 424/250 |
| 1071205 | 5/1976 | Canada ............................. | 544/241 |
| 0092945 | 11/1983 | European Pat. Off. . | |

*Primary Examiner*—Donald G. Daus
*Assistant Examiner*—G. Hendricks
*Attorney, Agent, or Firm*—Wenderoth, Lind & Ponack

[57] ABSTRACT

A hydrazinopyridazine compound represented by the formula

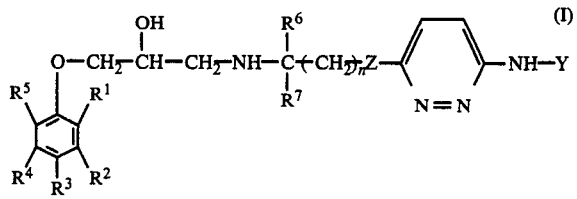

wherein $R^1$ represents a hydrogen atom, a halogen atom, a hydroxyl group, a cyano group, a lower alkyl group which may optionally be substituted by a halogen atom or a hydroxyl, lower alkoxy, lower alkylthio, lower alkanoylamino, allyloxy or tetrahydrofurfuryloxy group, a lower alkoxy group which may optionally be substituted by a 2-furyl, phenyl or lower alkoxy group, a lower alkenyl group, a lower alkenyloxy group, or a lower alkynyl group; $R^2$ represents a hydrogen atom, a halogen atom, a cyano group, a lower alkyl group which may optionally be substituted by a halogen atom or a lower alkoxy group, a lower alkoxy group, a lower alkenyl group, or a lower alkenyloxy group; $R^3$, $R^4$ and $R^5$, independently from each other, represent a hydrogen atom, a halogen atom, a lower alkyl group which may optionally be substituted by a lower alkoxy group, or a lower alkoxy group; $R^6$ and $R^7$, independently from each other, represent a hydrogen atom or a methyl group; Y represents $-NH_2$, $-NH-COOC_2H_5$, or

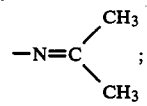

Z represents $-O-$, $-S-$, or

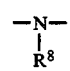

in which $R^8$ represents a hydrogen atom or a lower alkyl group; and n is 1 or 2, or its salt; a process for the production the aforesaid compounds; and use of such compounds as antihypertensive agents.

11 Claims, No Drawings

HYDRAZINOPYRIDAZINE COMPOUND, PROCESS FOR PRODUCTION THEREOF, AND USE THEREOF AS MEDICAMENT

This application is a continuation of now abandoned application Ser. No. 388,476, filed June 14, 1982.

This invention relates to a novel hydrazinopyridazine compound, and more specifically, to a hydrazinopyridazine compound represented by the following formula (I)

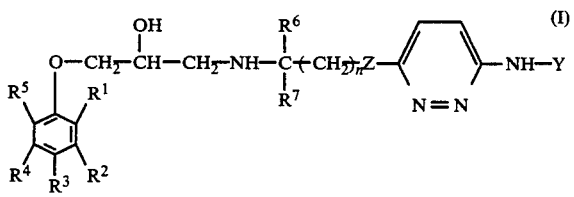

wherein $R^1$ represents a hydrogen atom, a halogen atom, a hydroxyl group, a cyano group, a lower alkyl group which may optionally be substituted by a halogen atom or a hydroxyl, lower alkoxy, lower alkylthio, lower alkanoylamino, allyloxy or tetrahydrofurfuryloxy group, a lower alkoxy group which may optionally be substituted by a 2-furyl, phenyl or lower alkoxy group, a lower alkenyl group, a lower alkenyloxy group, or a lower alkynyl group, $R^2$ represents a hydrogen atom, a halogen atom, a cyano group, a lower alkyl group which may optionally be substituted by a halogen atom or a lower alkoxy group, a lower alkoxy group, a lower alkenyl group, or a lower alkenyloxy group, $R^3$, $R^4$ and $R^5$, independently from each other, represent a hydrogen atom, a halogen atom, a lower alkyl group which may optionally be substituted by a lower alkoxy group, or a lower alkoxy group, $R^6$ and $R^7$, independently from each other, represent a hydrogen atom or a methyl group, Y represents $-NH_2$, $-NH-COOC_2H_5$, or

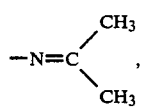

Z represents $-O-$, $-S-$, or

in which $R^8$ represents a hydrogen atom or a lower alkyl group, and n is 1 or 2;

and its salt.

The invention also pertains to a process for producing the aforesaid hydrazinopyridazine compounds or their salts and use of such compounds as antihypertensive agents.

A number of compounds having antihypertensive activity have been proposed up to date. Vasodilators frequently used in the clinical field as antihypertensive agents generally have a definite antihypertensive effect in most hypertensive patents, but their hypotensive action is relatively weak and furthermore they have the defect of inducing tachycardia. β-Adrenoceptor blocking agents have also been increasingly used in the treatment of hypertension for many years.

It is well known that their antihypertensive action is not powerful and sets in slowly. Unlike vasodilators, however, they have the advantage of not causing techycardia. Thus, a sufficient effect cannot always be expected by administering a β-adrenoceptor blocking agent or a vasodilator singly and from this viewpoint, reports have accumulated steadily of the effectiveness of combined therapy with these two types of agents in controlling hypertension. This practice is somewhat troublesome to patients and is not desirable for medication. Accordingly, if a single compound possessing β-adrenoceptor blocking and vasodilating activities is available, it would reduce the patient's compliance and make the treatment of hypertensive patients successful. It has therefore been desired to produce fascinating antihypertensive agents which show rapid and accurate antihypertensive activity without causing reflux tachycardia. Recently, some antihypertensive agents having both β-adrenoceptor blocking and vasodilating activities were proposed (see West German Offenlegungsschrift No. 2527066 and No. 2556918), although these patent documents give only a small amount of data concerning their β-adrenoceptor blocking and vasodilating activities.

The present inventors proposed a series of hydrazinopyradinol derivatives as antihypertensive agents free from the aforesaid defects in Japanese Laid-Open Patent Publication Nos. 142272/1981 and 169675/1981. On further investigations, the present inventors have discovered the compounds of formula (I) given above. The hydrazinopyridazine compounds of formula (I) described in this invention have not only β-adrenoceptor blocking action but also excellent vasodilating action as demonstrated by pharmacological data to be given hereinbelow (Tables 1 and 2). Some of them show a cardio-selective β-adrenoceptor blocking property. In view of the pharmacological feature and activity of these compounds, they seem to be very suitable and promising as antihypertensive agents.

Since the asterisked carbon atom in the compound of formula (I) shown below is an asymmetric carbon atom, it is evident that it can exist as an optically active or racemic form.

It should be understood therefore that the compounds of formula (I) embrace both of these optically active and racemic forms.

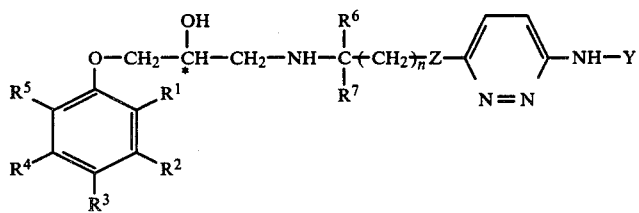

wherein $R^1$, $R^2$, $R^3$, $R^4$, $R^5$, $R^6$, $R^7$, Z, Y and n are as defined hereinabove.

The term "lower", as used herein to qualify a group or compound, means that the group or compound so qualified has not more than 5, preferably not more than 3, carbon atoms.

The lower alkyl group, as used herein, may be linear or branched, and includes, for example, methyl, ethyl, n- or iso-propyl, and n-, iso-, sec- or tert-butyl groups. Methyl and ethyl groups are suitable.

The lower alkoxy group includes, for example, methoxy, ethoxy, n-propoxy and isopropoxy groups.

Examples of the lower alkylthio groups are methylthio and ethylthio groups.

An acetylamino group is an example of the lower alkanoylamino group.

Examples of the lower alkenyl group are allyl and 1-propenyl groups, and the allyl group is preferred.

The lower alkenyloxy group is a lower alkenyl-O- group in which the lower alkenyl moiety is as described above. An allyloxy group is a preferred example.

Examples of the lower alkynyl group are ehtynyl and propargyl groups.

The halogen atom means fluorine, chlorine, bromine and iodine atoms. Fluorine, chlorine and bromine atoms are preferred.

The substituted lower alkyl group in the "lower alkyl group which may optionally be substituted by a halogen atom or a hydroxyl, lower alkoxy, lower alkylthio, lower alkanoylamino, allyloxy or tetrahydrofurfuryloxy group", the "lower alkyl group which may optionally be substituted by a halogen atom or a lower alkoxy group", and the "lower alkyl group which may optionally be substituted by a lower alkoxy group" include lower alkyl groups substituted by halogen atoms such as trifluoromethyl and trichloromethyl groups; and lower alkyl groups substituted by one of the other substituents mentioned above except halogen atoms, such as acetylaminomethyl, 2-acetylaminoethyl, hydroxymethyl, 2-hydroxyethyl, 3-hydroxypropyl, ethoxymethyl, 2-methoxyethyl, 2-ethoxyethyl, 3-methoxypropyl, ethylthiomethyl, 2-methylthioethyl, 2-tetrahydrofurfuryloxyethyl and 2-allyloxyethyl groups.

The substituted lower alkoxy group in the "lower alkoxy group which may optionally be substituted by a 2-furyl, phenyl or lower alkoxy group" includes, for example, furfuryloxy, benzyloxy, phenethyloxy, methoxymethoxy, 2-methoxyethoxy and 2-ethoxyethoxy groups.

Preferred examples of $R^1$ in formula (I) are a chlorine atom and methyl, trifluoromethyl, ethynyl, ethyl, methoxymethyl, 2-methoxyethyl, allyl and cyano groups, and the chlorine atom and methyl, trifluoromethyl and ethynyl groups are especially preferred. Preferred examples of $R^2$ are a chlorine atom, and methyl, cyano and trifluoromethyl groups, and the methyl and trifluoromethyl groups are especially preferred. A chlorine atom and a methyl group are preferred as $R^3$, $R^4$ and $R^5$.

A preferred group of compounds of formula (I) includes those compounds of formula (I) in which Z is an oxygen atom and/or $R^6$ and $R^7$ are both methyl groups, and/or n is 1, above all compounds of the following formula (I-a)

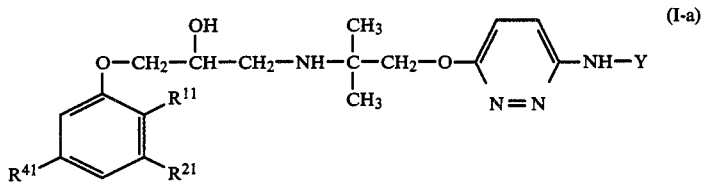

wherein $R^{11}$ represents a chlorine atom or a methyl, trifluoromethyl, ethynyl, ethyl, methoxymethyl, 2-methoxyethyl, allyl or cyano group, $R^{21}$ represents a chlorine atom or a methyl, cyano or trifluoromethyl group, $R^{41}$ represents a methyl group or a chlorine atom, provided that one of $R^{21}$ and $R^{41}$ represents a hydrogen atom, and Y is as defined above.

In formula (I-a), Y is preferably —NH$_2$.

Another preferred group of the hydrazinopyridazine compounds of formula (I) includes those of formula (I) in which $R^1$ represents a chlorine atom or a methyl, trifluoromethyl or ethynyl group, and $R^2$, $R^3$, $R^4$ and $R^5$ are hydrogen atoms; or $R^1$ represents a chlorine atom, one of $R^2$ and $R^4$ is a hydrogen atom and the other is a methyl group, and $R^3$ and $R^5$ are hydrogen atoms.

Typical examples of the hydrazinopyridazine compounds of formula (I) provided by this invention include the following compounds in addition to those given in Examples.

1-(2-Cyanophenoxy)-3-[1-methyl-2-(3-hydrazino-6-pyridazinyloxy)ethylamino]-2-propanol.
1-(2-allylphenoxy)-3-[1-methyl-2-(3-hydrazino-6-pyridazinyloxy)ethylamino]-2-propanol,
1-(2-bromo-3-methylphenoxy)-3-[1,1-dimethyl-2-(3-hydrazino-6-pyridazinyloxy)ethylamino]-2-propanol,
1-(2-bromo-5-methylphenoxy)-3-[1,1-dimethyl-2-(3-hydrazino-6-pyridazinyloxy)ethylamino]-2-propanol,
1-(2-chloro-3-methylphenoxy)-3-[1-methyl-2-(3-hydrazino-6-pyridazinyloxy)ethylamino]-2-propanol,
1-(2-methyl-5-chlorophenoxy)-3-[1,1-dimethyl-2-(3-hydrazino-6-pyridazinyloxy)ethylamino]-2-propanol,
1-(2-ethyl-3-chlorophenoxy)-3-[1,1-dimethyl-2-(3-hydrazino-6-pyridazinyloxy)ethylamino]-2-propanol,
1-(2-ethoxymethylphenoxy)-3-[1,1-dimethyl-2-(3-hydrazino-6-pyridazinyloxy)ethylamino]-2-propanol,
1-[2-(2-methoxyethyl)-5-chlorophenoxy]-3-[1,1-dimethyl-2-(3-hydrazino-6-pyridazinyloxy)ethylamino]-2-propanol,
1-[2-(2-methoxyethyl)phenoxy]-3-[1-methyl-2-(3-hydrazino-6-pyridazinyloxy)ethylamino]-2-propanol,
1-(2-methoxyphenoxy)-3-[1-methyl-2-(3-hydrazino-6-pyridazinyloxy)ethylamino]-2-propanol,
1-[2-(2-methoxyethoxy)phenoxy]-3-[1-methyl-2-(3-hydrazino-6-pyridazinyloxy)ethylamino]-2-propanol,
1-(2-ethoxymethoxyphenoxy)-3-[1,1-dimethyl-2-(3-hydrazino-6-pyridazinyloxy)ethylamino]-2-propanol,
1-(2-allylphenoxy)-3-[1-methyl-2-(3-hydrazino-6-pyridazinylthio)ethylamino]-2-propanol,
1-(2-chlorophenoxy)-3-[1,1-dimethyl-2-(3-hydrazino-6-pyridazinylthio)ethylamino]-2-propanol,
1-(2-propargylphenoxy)-3-[1,1-dimethyl-2-(3-hydrazino-6-pyridazinylthio)ethylamino]-2-propanol,
1-(2-cyanophenoxy)-3-[2-(3-hydrazino-6-pyridazinyloxy)-ethylamino]-2-propanol,
1-[2-(2-methoxyethyl)phenoxy]-3-[2-(3-hydrazino-6-pyridazinyloxy)ethylamino]-2-propanol,
1-[2-(3-methoxypropyl)phenoxy]-3-[1,1-dimethyl-2-(3-hydrazino-6-pyridazinyloxy)ethylamino]-2-propanol,
1-[2-(2ethoxyethyl)phenoxy]-3-[1,1-dimethyl-2-(3-hydrazino-6-pyridazinyloxy)ethylamino]-2-propanol,
1-[2-(2-methylthioethyl)phenoxy]-3-[1,1-dimethyl-2-(3-hydrazino-6-pyridaznyloxy)ethylamino]-2-propanol,
1-(2-allylphenoxy)-3-[3-(3-hydrazino-6-pyridazinyloxy)-propylamino]-2-propanol,
1-(2-chloro-5-methylphenoxy)-3-[1-methyl-3-(3-hydrazino-6-pyridazinyloxy)propylamino]-2-propanol,
1-(2-chloro-3-methylphenoxy)-3-[1-methyl-3-(3-hydrazino-6-pyridazinyloxy)propylamino]-2-propanol,
1-(3-methoxy-4-chlorophenoxy)-3-[1,1-dimethyl-2-(3-hydrazino-6-pyridazinyloxy)ethylamino]-2-propanol, and
1-[2-(3-hydroxypropyl)phenoxy]-3-[1,1,-dimethyl-2-(3-hydrazino-6-pyridazinyloxy)ethylamino]-2-propanol.

According to this invention, there is provided an acid addition salt of the hydrazinopyridazine compound of formula (I). Examples of the acid addition salt of the compound of formula (I) are salts of inorganic acids such as hydrochloric acid, hydrobromic acid, sulfuric acid, nitric acid and phosphoric acid, and salts of organic acids such as acetic acid, propionic acid, citric acid, lactic acid and tartaric acid. Those acid addition salts which are pharmaceutically acceptable are advantageous.

According to this invention, the hydrazinopyridazine compound of formula (I) or its salt can be produced by reacting a compound of the following formula (II)

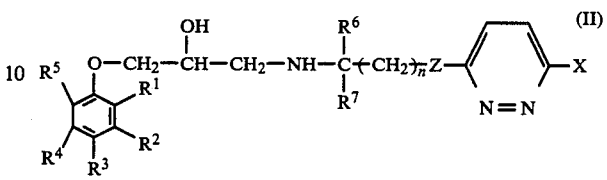

wherein $R^1$, $R^2$, $R^3$, $R^4$, $R^5$, $R^6$, $R^7$, Z and n are as defined above, and X represents a halogen atom, preferably a chlorine, bromine or iodine atom, especially preferably a chlorine atom,
with (a) hydrazine or hydrazine hydrate when Z in formula (II) represents —O— or —S—, or (b) ethyl carbazinate when Z in formula (II) represents

then as necessary, hydrolyzing the resulting compound of formula (I) in which Y is —NH—COOC$_2$H$_5$; then as necessary, reacting the resulting compound of formula (I) in which Y is —NH$_2$ with acetone; and as necessary converting the resulting compound of formula (I) to a salt.

The reaction of the compound of formula (II) in which Z is —O— or —S— [to be referred to hereinafter as the compound of formula (II-a)] with hydrazine or hydrazine hydrate, preferably the latter, can be carried out by contacting the reactants in the absence of a solvent or in the presence of an inert solvent. Examples of inert solvents which can be used include water; alcohols such as methanol, ethanol, propanol and isopropanol; ethers such as dioxane and tetrahydrofuran; organic bases such as pyridine and collidine; and aromatic hydrocarbons such as benzene, toluene and xylene.

The reaction temperature is not critical, and can be varied wiedly depending upon the type of the starring material of formula (II-a). Generally, it is advantageous that the reaction is carried out at a temperature of at least 20° C., preferably about 50° C. to the refluxing temperature of the reaction mixture.

The amount of hydrazine or its hydrate based on the compound of formula (II-a) is neither critical, and can be varied widely depending upon the type of the compound of formula (II-a) or the reaction conditions. Generally, it is at least 2 moles, preferably about 10 to about 200 moles, more preferably about 50 to about 100 moles, per mole of the compound of formula (II-a).

The reaction time varies depending upon the type of the compound of formula (II-a) or the reaction temperature. Usually, the reaction can be terminated in about 0.5 to about 10 hours.

The above reaction may be carried out in the presence of a suitable base. Examples of bases which can be used include alkali metal carbonates such as potassium carbonate and sodium carbonate; alkali metal hydroxides such as potassium hydroxide and sodium hydroxide; and organic bases such as pyrrolidine, piperazine, piperidine, morpholine and 4-dimethyl-aminopyridine. The base can be used in an amount of about 1 to about 100 equivalents, preferably about 1 to about 10 equivalents, per mole of the compound of formula (II-a). At this time, hydrazine or its hydrate may be used in a large excess so that the excess of hydrazine or its hydrate acts as a base.

By the above reaction, the compound of formula (I) in which Y is —NH$_2$, that is, a hydrazine derivative of formula (I-b) below, is obtained.

material of formula (II-b). Generally, it is about 80° to about 160° C., preferably about 120° to about 150° C.

The amount of ethyl carbazinate is not particularly restricted. Conveniently, it is generally about 1 to about 20 moles, preferably about 2 to about 10 moles, per mole of the compound of formula (II-b).

The reaction of the compound of formula (II-b) with ethyl carbazinate can be terminated in about 0.5 to about 3 hours under these conditions.

By the above reaction, the compound of formula (I) in which Y is —NH—COOC$_2$H$_5$, that is, a compound of the following formula (I-c), can be obtained.

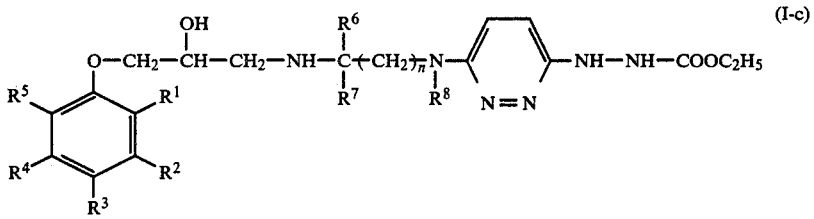

wherein $R^1$, $R^2$, $R^3$, $R^4$, $R^5$, $R^6$, $R^7$, $R^8$ and n are as defined hereinabove.

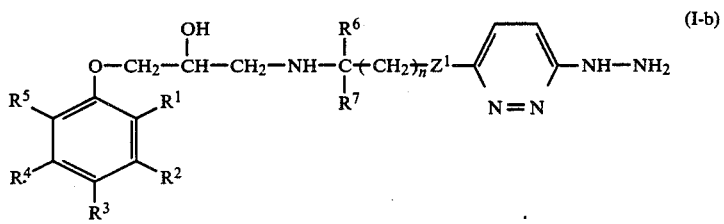

wherein $R^1$, $R^2$, $R^3$, $R^4$, $R^5$, $R^6$, $R^7$ and n are as defined hereinabove, and $Z^1$ represents —O— or —S—.

On the other hand, the reaction of the compound of formula (II) in which Z represents

[to be referred to hereinafter as the compound of formula (II-b)] with ethyl carbazinate can be carried out in the absence of a solvent or in the presence of an inert solvent. Examples of the inert solvent are alcohols such as propanol and butanol; ethers such as dioxane and tetrahydrofuran; aromatic hydrocarbons such as toluene, xylene and tetralin; and hydrocarbons such as cyclohexane and decalin.

The reaction temperature is not critical, and can be widely varied depending upon the type of the starting As required, the compound of formula (I-c) may be hydrolyzed to split off the carboethoxy group from the carboethoxyhydrazino group moiety to give a compound of the following formula

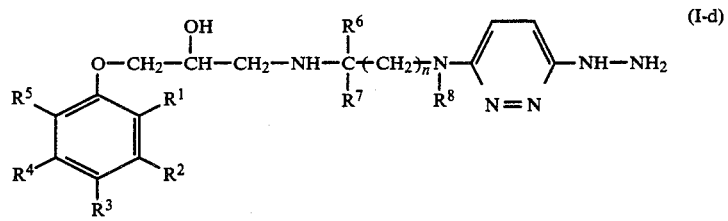

wherein all symbols are as defined.

Hydrolysis of the compound of formula (I-c) can be carried out by a method known per se, for example at room temperature to the refluxing temperature of the reaction mixture using an acid such as hydrochloric acid and hydrobromic acid.

As required, the resulting compound of formula (I-b) or (I-d) may be reacted with acetone to give a compound of formula (I) in which Y is

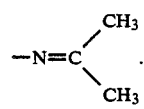

Conversion of the compound of formula (I-b) or (I-d) into a hydrazone compound by using acetone can be carried out by contacting the compound of formula (I-b) or (I-d) with acetone in the absence of a solvent or in the presence of an inert solvent. Examples of the inert solvent include water; alcohols such as methanol, ethanol and propanol; ethers such as diethyl ether, dioxane and tetrahydrofuran; aromatic hydrocarbons such as benzene, toluene and xylene; and halogenated hydrocarbons such as dichloromethane, chloroform and tetrachloroethane. The reaction proceeds sufficiently smoothly even at room temperature. If desired, the reaction may be carried out by heating the reactants to the refluxing temperature of the reaction mixture, preferably to a temperature below about 100° C.

The amount of acetone based on the compound of formula (I-b) or (I-d) is not critical, and can be varied widely depending upon the type of the compound of formula (I-b) or (I-d). Generally, it is advantageous to use acetone in an amount of at least 1 mole, preferably about 2 to about 100 moles, especially preferably about 10 to about 50 moles, per mole of the compound of formula (I-b) or (I-d).

This reaction proceeds very rapidly and almost quantitatively, and ends in about 10 to about 60 minutes.

Thus, the hydrazinopyridazine compound of formula (I) is obtained. It can be separated from the reaction mixture and/or can be purified by various known procedures such as extraction, column chromatography, thin-layer chromatography and recrystallization.

When both of $R^6$ and $R^7$ in the compound of formula (I) are methyl groups or hydrogen atoms, the racemic mixture can, as necessary, be separated into optically active forms by, for example, going through a diastereomer salt of the compound of formula (I), for example its salt with tartaric acid, malic acid, camphoric acid, camphorsulfonic acid, etc.

The aforesaid optical resolution may be applied to the starting compound of formula (II), and in this case, too, the aforesaid method of optical resolution can be used. By introducing the hydrazino group into the resulting optically active starting compound, it can be converted to an optically active compound of formula (I).

If further required, the hydrazinopyridazine compound of formula (I) can be converted to its salt by treating it in a customary manner with an inorganic acid such as hydrochloric acid, hydrobromic acid, sulfuric acid, nitric acid or phosphoric acid, or an organic acid such as acetic acid, propionic acid, citric acid, lactic acid or tartaric acid.

The compounds of formula (II) used as starting materials in the above process of this invention are novel. Typical examples include the following compounds in addition to those given in Examples.

1-(2-Cyanophenoxy)-3-[1,1-dimethyl-2-(3-bromo-6-pyridazinyloxy)ethylamino]-2-propanol,
1-(2-allylphenoxy)-3-[1-methyl-2-(3-chloro-6-pyridazinyloxy)ethylamino]-2-propanol,
1-(2-chloro-3-methylphenoxy)-3-[1,1-dimethyl-2-(3-bromo-6-pyridazinyloxy)ethylamino]-2-propanol,
1-(2-chloro-5-methylphenoxy)-3-[1,1-dimethyl-2-(3-bromo-6-pyradinyloxy)ethylamino]-2-propanol,
1-(2-bromo-3-methylphenoxy)-3-[1,1-dimethyl-2-(3-chloro-6-pyridazinyloxy)ethylamino]-2-propanol,
1-(2-ethyl-3-chlorophenoxy)-3-[1,1-dimethyl-2-(3-chloro-6-pyridazinyloxy)ethylamino]-2-propanol,
1-[2-(2-methoxyethyl)phenoxy]-3-[1,1-dimethyl-2-(3-bromo-6-pyridazinyloxy)ethylamino]-2-propanol,
1-(2-ethoxymethylphenoxy)-3-[1,1-dimethyl-2-(3-chloro-6-pydirazinyloxy)ethylamino]-2-propanol,
1-[2-(2-methoxyethyl)phenoxy]-3-[1-methyl-2-(3-chloro-6-pyridazinyloxy)ethylamino]-2-propanol,
1-(2-methoxyphenoxy)-3-[1-methyl-2-(3-chloro-6-pyridazinyloxy)ethylamino]-2-propanol,
1-(2-cyanophenoxy)-3-[1,1-dimethyl-2-(3-chloro-6-pyridazinylthio)ethylamino]-2-propanol,
1-(2-allylphenoxy)-3-[1-methyl-2-(3-chloro-6-pyridazinylthio)ethylamino]-2-propanol, and
1-[2-(2-methoxyethyl)phenoxy]-3-[1,1-dimethyl-2-(3-bromo-6-pyridazinylthio)ethylamino]-2-propanol.

These compounds of formula (II) can be synthesized by the process shown in Scheme A when Z is —O— or —S—, and by the process shown in Scheme B when Z is $$-\underset{R^8}{N}-.$$

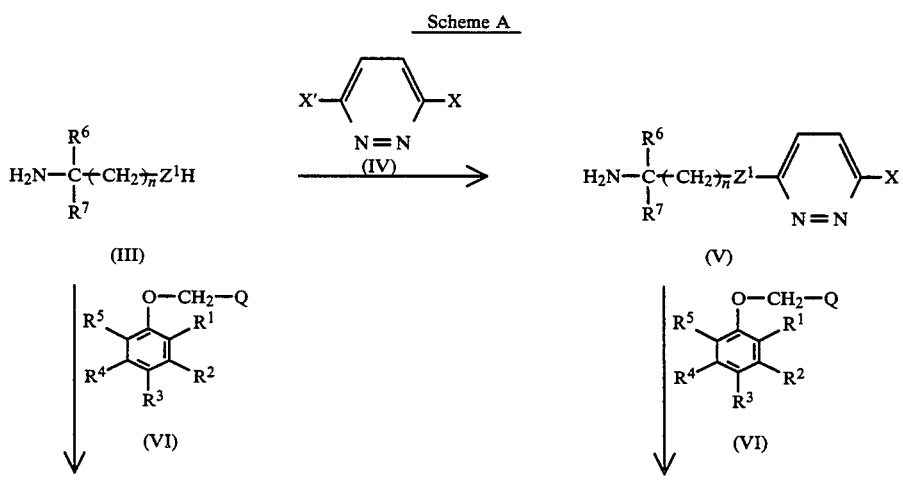

Scheme A

-continued
Scheme A

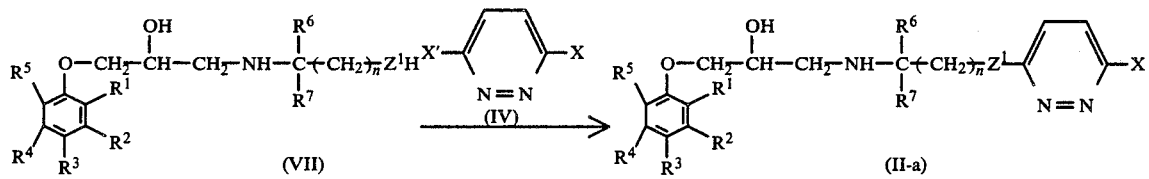

In Scheme A, $R^1$, $R^2$, $R^3$, $R^4$, $R^5$, $R^6$, $R^7$, $Z^1$, n and X are as defined hereinabove; X' represent a halogen atom which is identical with or different from X; and Q represents

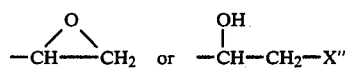

in which X" represents a halogen atom.

According to a first embodiment in Scheme A, the compound of formula (IV) known per se is reacted with the compound of formula (III). This reaction can be carried out by using the compound (III) in the form of an alkoxide or alkylsulfide corresponding to formula (III) in which —$Z^1$H changes to —$Z^1$M wherein M is an alkali metal (for example, a sodium alkoxide, a potassium alkoxide or a sodium alkylsulfide), or using the compound (III) in the presence of a base such as sodium hydride, sodium amide, sodium hydroxide, potassium hydroxide or lithium hydroxide, and contacting it with the compound (IV). The reaction can be carried out in the absence of a solvent, or preferably in the presence of an inert solvent, for example an aromatic hydrocarbon (e.g., benzene, toluene or xylene), an ether (e.g., dioxane, tetrahydrofuran, diethyl ether or dimethoxyethane), an amide such as dimethylformamide, or an organic base (e.g., pyridine, triethylamine or dimethylaniline) at a temperature of from 0° C. to the refluxing temperature of the reaction mixture, preferably from room temperature to the refluxing temperature of the reaction mixture.

The proportions of the compounds of formulae (IV) and (III) are not particularly restricted. Advantageously, at least 1 mole, preferably about 1 to about 2 moles, of the compound (III) is used per mole of the compound (IV). Under these reaction conditions, the reaction can be terminated in about 0.5 to 5 hours.

Thus, the compound of formula (V) can be obtained in good yields. This compound is novel, too. Typical examples of the compound (V) are 3-(2-amino-2-methylpropoxy)-6-chloropyridazine, 3-(2-amino-2-methylpropylthio)-6-chloropyridazine, 3-(2-aminopropoxy)-6-chloropyridazine, 3-(2-aminopropylthio)-6-chloropyridazine, 3-(2-aminoethoxy)-6-chloropyridazine, and 3-(2-amino-2-methylpropoxy)-6-bromopyridazine.

The compound of formula (II) can be produced by reacting the compound of formula (V) with the compound of formula (VI). This reaction can be easily carried out by contacting the compound (V) and the compound (VI) in the presence or absence of a solvent, preferably in the presence of an inert organic solvent. The reaction temperature is not critical, and can be properly selected. Generally, it is about 0° C. to about 200° C., preferably from room temperature to about 100° C. In the present reaction, about 1 to about 2 moles of the compound (V) can be used per mole of the compound (VI).

The reaction time can be properly varied depending upon the type of the reactants, the reaction temperature, etc., and is generally from about 1 to 5 hours.

Examples of inert solvents which can be used in the aforesaid reaction include water; lower alcohols such as methanol, ethanol and isopropanol; aromatic hydrocarbons such as benzene, xylene and toluene; and halogenated hydrocarbons such as chloroform, dichloromethane, dichloroethane, trichloroethane and carbon tetrachloride.

The compound (VI) in which Q is

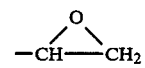

in the first embodiment described above is obtained, for example, by reacting a compound of the following formula (VIII)

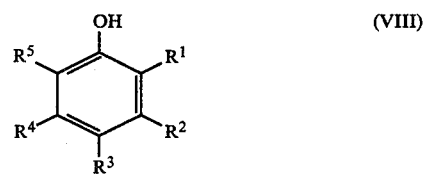

wherein $R^1$, $R^2$, $R^3$, $R^4$ and $R^5$ are as defined hereinabove, with an epihalohydrin. By treating the resulting compound (VI) in which Q is

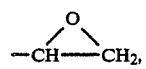

that is, a compound of the following formula (VI-a)

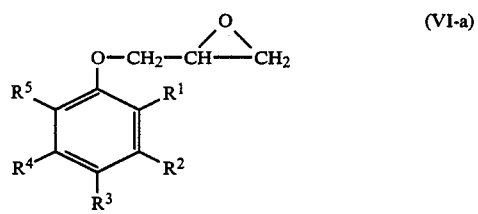

wherein $R^1$, $R^2$, $R^3$, $R^4$ and $R^5$ are as defined above, with a hydrohalic acid (HX") to cleave the epoxy group, a compound of formula (VI) in which Q represents

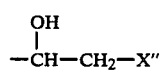

can be produced.

The reaction of the compound (VIII) with an epihalohydrin can be carried out in a customary manner, for example at room temperature to about 100° C., preferably in the absence of a solvent or in the presence of water or an alcohol such as methanol, ethanol or propanol, for about 1 to about 5 hours under alkaline conditions. This reaction can give the desired product (VI-a) in good yields.

The reaction of cleaving the epoxy group of the compound (VI-a) with a hydrohalic acid such as hydrochloric acid or hydrobromic acid can be carried out in a customary manner, for example at 0° C. to the refluxing temperature of the reaction mixture, preferably in the presence of an inert organic solvent such as chloroform, ethanol, benzene or dioxane, for a period of about 0.5 to about 5 hours.

According to a second embodiment in Scheme A, the compound of formula (III) is reacted with the compound of formula (VI). This reaction can be carried out in the same way as described above with regard to the reaction of the compounds (V) and (VI).

Thus, the compound of formula (VII) is obtained.

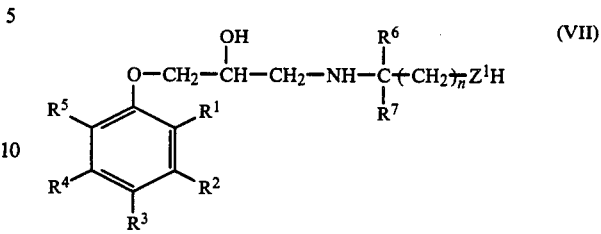

wherein all symbols are as defined above. This compound (VII) can be converted to the compound of formula (II) by reacting it with the compound (IV).

The reaction of the compound (VII) with the compound (IV) can be carried out in the same way as described hereinabove in regard to the reaction of the compound (III) with the compound (IV) in the first embodiment.

The compound of formula (II) produced by the first or second embodiment is usually separated from the reaction mixture by methods known per se, and then used for reaction with hydrazine or its hydrate.

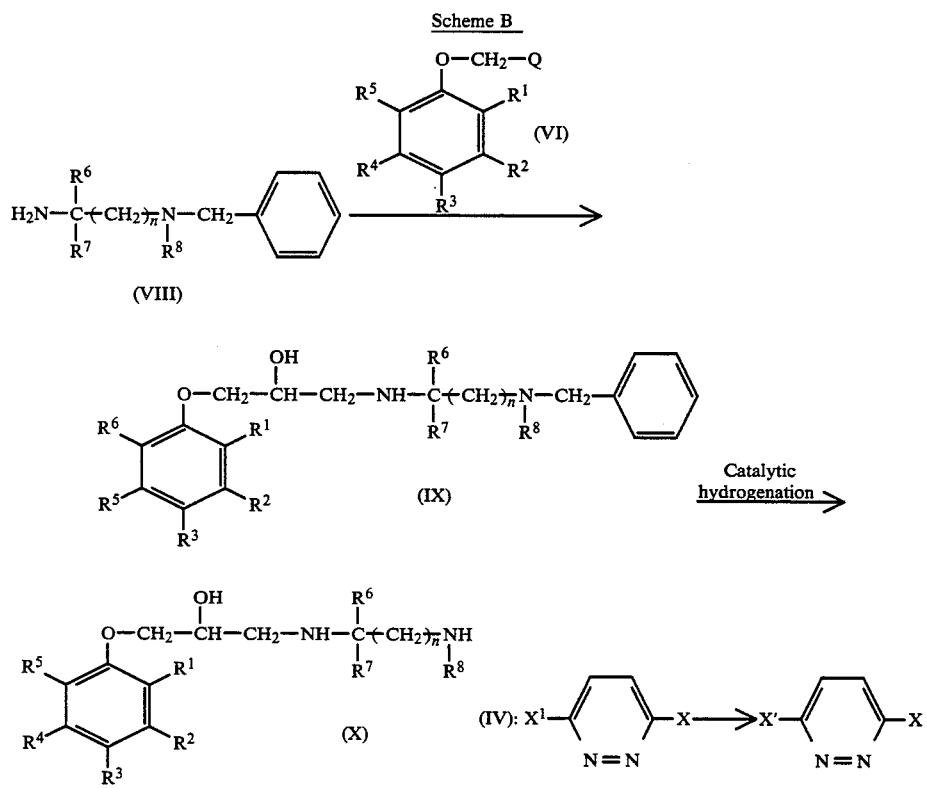

Scheme B

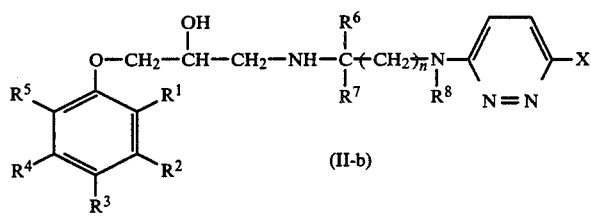

(II-b)

In Scheme B, all symbols are as defined hereinabove.

In Scheme B, the reaction of the compound of formula (VIII) with the compound of formula (VI) can be carried out under the same conditions as described above with regard to the reaction of the compound (III) with the compound (VI).

The resulting compound of formula (IX) is then catalytically hydrogenated to form the compound of formula (X). Hydrogenation can be performed by contacting the compound (IX) with a hydrogen gas at atmospheric pressure to an elevated pressure of up to about 100 atmospheres in the presence of a hydrogenation catalyst such as palladium-carbon, palladium black, platinum black or Raney nickel in a suitable inert solvent, for example an alcohol such as methanol, ethanol or propanol, an ether such as dioxane or tetrahydrofuran, a halogenated hydrocarbon such as chloroform or dichloromethane, or an acid such as dilute hydrochloric acid or acetic acid.

By the hydrogenation, the benzyl group is split off from the compound (IX), and the compound (X) results.

The compound (X) is then reacted with the compound of formula (IV). This reaction can be carried out in the absence of a solvent or in the presence of an inert solvent, for example an alcohol such as propanol or butanol, an ether such as dioxane or tetrahydrofuran, or an aromatic hydrocarbon such as toluene or xylene at a temperature of generally about 0° C. to the refluxing temperature of the reaction mixture, preferably at a temperature of from 50° to 120° C. The proportions of the compounds (X) and (IV) are not critical, and can be widely changed according to the types of these compounds, etc. Conveniently, the compound (IV) is used in an amount of generally at least 1 mole, preferably about 2 to about 4 moles, per mole of the compound (X).

Thus, the compound of formula (II-b) can be obtained. This compound can usually be separated from the reaction mixture by methods known per se, and then used for reaction with ethyl carbazinate.

To evaluate the activities of the compounds of formula (I) provided by this invention, the following experiments were performed.

The following compounds were submitted to animal experiments.

A: 1-phenoxy-3-[1,1-dimethyl-2-(3-hydrazino-6-pyridazinyloxy)ethylamino]-2-propanol B: 1-(2-chlorophenoxy)-3-[1,1-dimethyl-2-(3-hydrazino-6-pyridazinyloxy)ethylamino]-2-propanol C: 1-(2-methylphenoxy)-3-[1,1-dimethyl-2-(3-hydrazino-6-pyridazinyloxy)ethylamino]-2-propanol D: 1-(2-ethylphenoxy)-3-[1,1-dimethyl-2-(3-hydrazino-6-pyridazinyloxy)ethylamino]-2-propanol E: 1-(2-propylphenoxy)-3-[1,1-dimethyl-2-(3-hydrazino-6-pyridazinyloxy)ethylamino]-2-propanol F: 1-(2-chloro-3-methylphenoxy)-3-[1,1-dimethyl-2-(3-hydrazino-6-pyridazinyloxy)ethylamino]-2-propanol G: 1-(2-chloro-5-methylphenoxy)-3-[1,1-dimethyl-2-(3-isopropylidenehydrazino-6-pyridazinyloxy)ethylamino]-2-propanol H: 1-(2-chloro-5-methylphenoxy)-3-[1,1-dimethyl-2-(3-hydrazino-6-pyridazinyloxy)ethylamino]-2-propanol I: 1-(2-cyanophenoxy)-3-[1,1-dimethyl-2-(3-hydrazino-6-pyridazinyloxy)ethylamino]-2-propanol J: 1-(2-cyano-5-chlorophenoxy)-3-[1,1-dimethyl-2-(3-hydrazino-6-pyridazinyloxy)ethylamino]-2-propanol K: 1-(2-cyano-5-methylphenoxy)-3-[1,1-dimethyl-2-(3-hydrazino-6-pyridazinyloxy)ethylamino]-2-propanol L: 1-(2-methoxymethylphenoxy)-3-[1,1-dimethyl-2-(3-hydrazino-6-pyridazinyloxy)ethylamino]-2-propanol M: 1-(2-ethoxymethylphenoxy)-3-[1,1-dimethyl-2-(3-hydrazino-6-pyridazinyloxy)ethylamino]-2-propanol N: 1-[2-(2-methoxyethyl)phenoxy]-3-[1,1-dimethyl-2-(3-hydrazino-6-pyridazinyloxy)ethylamino]-2-propanol O: 1-[2-(2-ethoxyethyl)phenoxy]-3-[1,1-dimethyl-2-(3-hydrazino-6-pyridazinyloxy)ethylamino]-2-propanol P: 1-(2-allyloxyphenoxy)-3-[1,1-dimethyl-2-(3-hydrazino-6-pyridazinyloxy)ethylamino]-2-propanol Q: 1-(2-methylphenoxy)-3-[1,1-dimethyl-2-(3-hydrazino-6-pyridazinylthio)ethylamino]-2-propanol R: 1-(2-ethinylphenoxy)-3-[1,1-dimethyl-2-(3-hydrazino-6-pyridazinyloxy)ethylamino]-2-propanol

Testing methods

Experiments were done using male Wistar rats weighing between 300 and 400 g, anesthetized with sodium pentobarbital (60 mg/kg i.p.). The blood pressure was directly measured by connecting a cannula inserted in the femoral artery to a pressure transducer and the heart rate was calculated from the pulse waves of the blood pressure tracings. Each value shown here was obtained from three animals. The test compounds were individually dissolved in physiological saline solution or a 0.01N aqueous solution of hydrochloric acid.

(1) Measurement of β-adrenoceptor blocking activity

A single intravenous (i.v.) injection of isoproternol (0.1 μg/kg) produced an increase in heart rate by approximately 90 beats/min. The increased heart rate before injection of the test compound was represented by $H_1$. Three minutes after i.v. injection of the test compound, isoproterenol (0.1 μg/kg i.v.) was again administered and then the change in heart rate was measured. The maximum increase in heart rate after injection of the test compound was designated as $H_2$.

From these values, the percent inhibition of the change in heart rate was calculated in accordance with the following equation.

Percent inhibition of the heart rate $= 100 - (H_2/H_1) \times 100$

By repeating the procedure mentioned above at various doses of the test compounds, dose-response curves were prepared. From these curves, their respective ID$_{50}$ values (doses of test compounds required for 50% inhibition of responses to isoproterenol) were determined. The results are shown in Table 1. In order to examine the selectivity of β-adrenoceptor blocking action of these test compounds, their blocking activity ratios ($\beta_1/\beta_2$) were calculated from the doses required for causing a 50% inhibition of a fall in blood pressure ($\beta_2$) and an increase in heart rate ($\beta_1$) exerted by isoproterenol (0.1 μg/kg i.v.). The results are shown in Table 2.

(2) Measurement of vasodilating activity (Hypotensive activity)

Each test compound dissolved in physiological saline solution or 0.01N hydrochloric acid was intravenously injected into rats in a fixed dose of 1 mg/kg and the blood pressure was continuously monitored for 40 minutes. The maximum fall in blood pressure during this period was determined and taken as the hypotensive activity of each compound. The results are shown in Table 1.

TABLE 1

| Compound | β-adrenoceptor blocking action ID$_{50}$ (mg/kg i.v.) | Hypotensive action |
|---|---|---|
| A | 0.04 | ++ |
| B | 0.008 | +++ |
| C | 0.015 | +++ |
| D | 0.2 | +++ |
| E | 0.2 | ++ |
| F | 0.08 | ++ |
| G | 0.15 | ++ |
| H | 0.15 | ++ |
| I | 0.02 | +++ |
| J | 0.12 | ++ |
| K | 0.05 | +++ |
| L | 0.03 | +++ |
| M | 0.06 | ++ |
| N | 0.08 | +++ |
| O | 0.16 | ++ |
| P | 0.1 | ++ |
| Q | 0.04 | ++ |
| R | 0.02 | +++ |

TABLE 2

| Compound | β-adrenoceptor blocking action ID$_{50}$ (mg/kg i.v.) | | Selectivity for $\beta_1$-adrenoceptors ($\beta_1/\beta_2$) |
|---|---|---|---|
| | $\beta_1$ | $\beta_2$ | |
| B | 0.008 | 0.23 | 29 |
| C | 0.015 | 0.45 | 30 |
| I | 0.02 | 0.1 | 5 |
| K | 0.05 | 0.1 | 2 |
| R | 0.02 | No antagonistic action at 0.1 | >5 |
| Propranolol | 0.02 | 0.03 | 1.5 |
| Atenolol | 0.05 | 1.5 | 30 |

In Table 1, the marks, ++ and +++, represent a fall in blood pressure of 25 to 34 mmHg, and 35 mmHg or more, respectively.

Thus, the hydrazinopyridazine compounds of formula (I) provided by this invention are novel β-adrenoceptor blocking agents with potent vasodilating activity and some of them also possess cardio-selective ($\beta_1$-type) β-adrenoceptor blocking property. Accordingly, they can be used as antihypertensive agents for man and warm-blooded animals and, for this purpose, administered orally or parenterally (e.g., intramuscularly, intravenously, subcutaneously, intrarectally, sublingually, etc.).

When used as antihypertensive agents, the compounds (I) of this invention can be formulated into various forms suitable for oral or parenteral administration. For example, they can be formed into drugs by using nontoxic additives usually empoyed in this type of drugs, such as vehicles, binders, lubricants, disintegrants, antiseptics, isotonic agents, stabilizers, dispersants, antioxidants, coloring agents, flavoring agents, and buffers.

Depending upon the intended use, these drugs may take various forms, for example solids (e.g., tablets, hard capsules, soft capsules, granules, powders, pellets, pills, and trouches), semisolids (e.g. suppositories), and liquids (injectable preparations, emulsions, suspensions and syrups).

Examples of the nontoxic additives mentioned above include starch, gelatin, glucose, lactose, fructose, maltose, magnesium carbonate, talc, magnesium stearate, methyl cellulose, carboxymethyl cellulose or its salt, gum arabic, polyethylene glycol, alkyl p-hydroxybenzoates, syrup, ethanol, propylene glycol, Vaseline, carbowax, glycerol, sodium chloride, sodium sulfite, sodium phosphate and citric acid.

The above drugs may also contain therapeutically useful other drugs.

The content of the compound (I) of this invention in the drugs may vary depending upon its form. Generally, it is preferably 5 to 100% by weight in the case of solid and semisolid drugs, and 0.1 to 10% by weight in the case of liquid drugs.

The dose of the compound (I) of this invention can be varied widely depending upon the type of the subject, the severity of the subject's condition, a physician's diagnosis, etc. Generally, it is 0.02 to 30 mg/kg, preferably 0.05 to 10 mg/kg, per day. The dose may be below or above the specified limit depending upon the severity of the condition of the patient, and the diagnosis of a physician. The above daily dose may be given at a time or in two or more divided portions.

The following Examples illustrate the present invention more specifically.

NMR spectra were measured with Hitachi R-20A (60M Hz) using tetramethylsilane as an internal standard in CDCl$_3$ and CD$_3$OD, and sodium 2-dimethyl-2-silapentane-5-sulfonate in D$_2$O.

EXAMPLE 1

(a) To a suspension of 1.5 g of 61% sodium hydride in 20 ml of benzene was added dropwise at room temperature 2.7 g of 2-amino-2-methylpropanol, and then a solution of 4.5 g of 3,6-dichloropyridazine in 20 ml of benzene was added. The mixture was refluxed for one hour. The reaction mixture was cooled, washed with water, and dried over magnesium sulfate. The solvent was evaporated to give 4.33 g of 3-(2-amino-2-methylpropoxy)-6-chloropyridazine.

NMR (CDCl$_3$) δ: 1.22 (6H, s), 1.49 (2H, s), 4.23 (2H, s), 7.03 (1H, d, J=9 Hz), 7.42 (1H, d, J=9 Hz).

(b) A solution of 17.0 g of the 3-(2-amino-2-methylpropoxy)-6-chloropyridazine obtained in (a) above and 14.6 g of 1-(2-cyanophenoxy)-2,3-epoxypropane in 20 ml of methanol were refluxed for 4 hours. The solvent was evaporated under reduced pressure. A solution of the residue in 200 ml of benzene was extracted with 150 ml of 10% hydrochloric acid. The aqueous layer was made alkaline with 10% sodium hydroxide, and extracted with chloroform. The chloroform layer was dried over sodium sulfate. The solvent was evaporated, and the resulting oil was chromatographed on a column of Wakogel C-200 (100 g). From a fraction eluted with chloroform-methanol (30:1), 24.97 g of 1-(2-cyanophenoxy)-3-[1,1-dimethyl-2-(3-chloro-6-pydirazinyloxy)-ethylamino]-2-propanol was obtained as a pale yellow oil.

NMR(CDCl$_3$) δ: 1.21 (6H, s), 2.64 (2H, broad s), 2.73-2.96 (2H, m), 4.07 (3H, broad s), 4.32 (2H, s), 6.82-7.18 (2H, m), 6.98 (1H, d, J=9 Hz), 7.22-7.68 (2H, m), 7.33 (1H, d, J=9 Hz).

(c) A mixture of 900 mg of 1-(2-cyanophenoxy)-3-[1,1-dimethyl-2-(3-chloro-6-pyridazinyloxy)ethylamino]-2-propanol obtained in (b) above, 18 ml of hydrazine hydrate and 18 ml of ethanol was refluxed for 5 hours. The solvent was removed under reduced pressure. A solution of the residue in chloroform was washed with water and dried over magnesium sulfate. The solvent was evaporated under reduced pressure. A solution of the resulting oil in acetone was allowed to stand for 30 minutes at room temperature. The product was purified by thin-layer chromatography [silica gel (Merck GF$_{254}$); chloroform/methanol=10/1] to give 270 mg of a yellow oil. The oil was dissolved in acetone, and the solution was allowed to stand for 30 minutes at room temperature to give 150 mg of 1-(2-cyanophenoxy)-3-[1,1-dimethyl-2-(3-isopropylidenehydrazino-6-pyridazinyloxy)ethylamino]-2-propanol as yellow crystals having a melting point of 126° to 128° C.

NMR(CDCl$_3$) δ: 1.21 (6H, s), 1.91 (3H, s), 2.22 (3H, s), 2.30-3.25 (2H, m), 2.74-2.98 (2H, m), 4.08 (3H, broad s), 4.22 (2H, s), 6.82-7.13 (2H, m), 6.91 (1H, d, J=9 Hz), 7.20-7.67 (2H, m), 7.49 (1H, d, J=9 Hz).

(d) A mixture of 900 mg of 1-(2-cyanophenoxy)-3-[1,1-dimethyl-2-(3-isopropylidenehydrazino-6-pyridazinyloxy)ethylamino]-2-propanol obtained in (c) above, 6 ml of hydrazine hydrate and 30 ml of ethanol was refluxed for 2 hours. After evaporating the solvent under reduced pressure, a solution of the residue in chloroform was washed with water and dried over magnesium sulfate. The solvent was evaporated under reduced pressure. The residue was dissolved in ethanol, and 2 ml of 2N hydrochloric acid was added. The solvent was evaporated under reduced pressure. A solution of the residue in ethanol was kept at 0° C. overnight to give 684 mg of 1-(2-cyanophenoxy)-3-[1,1-dimethyl-2-(3-hydrazino-6-pyridazinyloxy)ethylamino]-2-propanol hydrochloride having a melting point of 184.1° to 187.6° C.

NMR(D$_2$O) δ: 1.59 (6H, s), 3.30-3.58 (2H, m), 4.19-4.60 (3H, m), 4.46 (2H, s), 6.98-7.82 (4H, m), 7.33 (2H, s).

EXAMPLE 2

(a) A solution of 6.04 g of 3-(2-amino-2-methylpropoxy)-6-chloropyridazine obtained in Example 1, (a) and 5.95 g of 1-(2-chloro-3-methylphenoxy)-2,3-epoxypropane in 120 ml of methanol was refluxed for 3 hours. The solvent was evaporated under reduced pressure. A solution of the residue in benzene was extracted with 175 ml of 0.2N hydrochloric acid. The aqueous layer was made alkaline with potassium carbonate and extracted with chloroform. The chloroform layer was dried over sodium sulfate. The solvent was evaporated and the residue (10 g) was purified by column chromatography (50 g of Florisil; eluted with chloroform) to give 7.98 g of 1-(2-chloro-3-methylphenoxy)-3-[1,1-dimethyl-2-(3-chloro-6-pyridazinyloxy)ethylamino]-2-propanol as a colorless oil.

NMR(CDCl$_3$) δ: 1.22 (6H, s), 2.36 (3H, s), 2.74 (2H, broad s), 2.79-3.02 (2H, m), 4.00 (3H, broad s), 4.32 (2H, s), 6.62-7.31 (3H, m), 6.90 (1H, d, J=9 Hz), 7.29 (1H, d, J=9 Hz).

(b) A mixture of 1.4 g of 1-(2-chloro-3-methylphenoxy)-3-[1,1-dimethyl-2-(3-chloro-6-pyridazinyloxy)ethylamino]-2-propanol obtained in (a) above, 14 ml of hydrazine hydrate and 14 ml of ethanol was refluxed for 5 hours with stirring. The solvent was distilled off under reduced pressure. The residue was dissolved in chloroform, washed with water and dried over magnesium sulfate. After distilling off the solvent, the residue was dissolved in acetone, and the solution was allowed to stand for 30 minutes at room temperature. The resulting hydrazone compound was separated by thinlayer chromatography [silica gel (Merck GF$_{254}$; chloroform/methanol=10/1] to give 374 mg of 1-(2-chloro-3-methylphenoxy)-3-[1,1-dimethyl-2-(3-isopropylidenehydrazino-6-pyridazinyloxy)ethylamino]-2-propanol as a yellow oil.

NMR(CDCl$_3$) δ: 1.22 (6H, s), 1.92 (3H, s), 2.02 (3H, s), 2.36 (3H, s), 2.70-3.20 (2H, m), 2.80-3.00 (2H, m), 4.03 (3H, broad s), 4.23 (2H, s), 6.60-7.30 (3H, m), 6.88 (1H, d, J=9 Hz), 7.49 (1H, d, J=9 Hz).

(c-1) A mixture of 1.12 g of 1-(2-chloro-3-methylphenoxy)-3-[1,1-dimethyl-2-(3-isopropylidenehydrazino-6-pyridazinyloxy)ethylamino]-2-propanol obtained in (b) above, 12 ml of hydrazine hydrate and 24 ml of ethanol was refluxed for 1.5 hours. After evaporating the solvent under reduced pressure, the residue was dissolved in chloroform. The solution was washed with water, and dried over magnesium sulfate. The solvent was evaporated and to a solution of the residue in ethanol was added 12 ml of 1n hydrochloric acid. The solvent was removed under reduced pressure. A solution of the residue in ethanol was left at 0° C. overnight to give 675 mg of 1-(2-chloro-3-methylphenoxy)-3-[1,1-dimethyl-2-(3-hydrazino-6-pyridazinyloxy)ethylamino]-2-propanol hydrochloride as colorless crystals having a melting point of 192° to 194° C.

NMR(D$_2$O) δ: 1.60 (6H, s), 2.30 (3H, s), 3.35–3.61 (2H, m), 4.14–4.38 (3H, m), 4.44 (2H, s), 6.78–7.47 (3H, m), 7.12 (2H, s).

(c-2) A mixture of 8 g of 1-(2-chloro-3-methylphenoxy)-3-[1,1-dimethyl-2-(3-chloro-6-pyridazinyloxy)ethylamino]-2-propanol obtained in (a) above, 160 ml of hydrazine hydrate and 160 ml of ethanol was refluxed for 7 hours with stirring. The solvent was evaporated under reduced pressure. A solution of the residue in benzene was extracted with 1N hydrochloric acid. The aqueous layer was made alkaline with potassium carbonate and extracted with chloroform. The chloroform layer was dried over sodium sulfate. The solvent was evaporated under reduced pressure to give 5.7 g of a crude product. To a solution of the crude product in 50 ml of ethanol was added 8 g of conc. hydrochloric acid. After removing the solvent under reduced pressure, a solution of the residue in ethanol was left at 0° C. overnight. Recrystallization of the product from ethanol gave 1.03 g of 1-(2-chloro-3-methylphenoxy)-3-[1,1-dimethyl-2-(3-hydrazino-6-pyridazinyloxy)ethylamino]-2-propanol hydrochloride as colorless crystals having a melting point of 192° to 194° C.

EXAMPLE 3

(a) A solution of 4.6 g of 3-(2-amino-2-methylpropoxy)-6-chloropyridazine obtained in Example 1 (a) and 5.0 g of 1-(2-chloro-5-methylphenoxy)-2,3-epoxypropane in 50 ml of ethanol was refluxed for 4 hours. The solvent was evaporated under reduced pressure a solution of the residue in 100 ml of benzene was extracted with 30 ml of 10% hydrochloric acid. The aqueous layer was made alkaline with 10% sodium hydroxide and extracted with chloroform, and the organic layer was dried over magnesium sulfate. The solvent was evaporated and the residue was chromatographed on a column of Florisil (50 g) using chloroform as an eluent. From the eluate was obtained 5.7 g of 1-(2-chloro-5-methylphenoxy)-3-[1,1-dimethyl-2-(3-chloro-6-pyridazinyloxy)ethylamino)-2-propanol as a colorless oil.

NMR(CDCl$_3$) δ: 1.20 (6H, s), 2.30 (3H, s), 2.75–3.10 (2H, m), 2.92 (2H, broad s), 4.00 (3H, broad s), 4.32 (2H, s), 6.68 (1H, d, J=6 Hz), 6.72 (1H, s), 6.92 (1H, d, J=9 Hz), 7.17 (1H, d, J=6 Hz), 7.30 (1H, d, J=9 Hz).

(b) A mixture of 740 mg of 1-(2-chloro-5-methylphenoxy)-3-[1,1-dimethyl-2-(3-chloro-6-pyridazinyloxy)ethylamino]-2-propanol obtained in (a) above, 15 ml of hydrazine hydrate and 15 ml of ethanol was refluxed overnight with stirring. The solvent was removed under reduced pressure. A solution of the residue in 90 ml of acetone was refluxed for 15 minutes. The solvent was evaporated. A solution of the residue in dichloromethane was washed successively with 5% sodium carbonate and an aqueous solution of sodium chloride, and dried over magnesium sulfate. After evaporating the solvent, the residue was purified by thin-layer chromatography [silica gel (Merck GF$_{254}$); chloroform/methanol=9/1] to give 252 mg of 1-(2-chloro-5-methylphenoxy)-3-[1,1-dimethyl-2-(3-isopropylidenehydrazino-6-pyridazinyloxy)ethylamino]-2-propanol as a pale yellow oil.

NMR(CD$_3$OD) δ: 1.21 (6H, s), 1.94 (3H, s), 2.00 (3H, s), 2.28 (3H, s), 2.74–2.96 (2H, m), 4.00 (3H, broad s), 4.19 (2H, s), 6.68 (1H, q, J=7 Hz, J=1 Hz), 6.81 (1H, d, J=1 Hz), 7.16 (1H, d, J=7 Hz), 6.92 (1H, d, J=9 Hz), 7.42 (1H, d, J=9 Hz).

(c) A mixture of 5.7 g of 1-(2-chloro-5-methylphenoxy)-3-[1,1-dimethyl-2-(3-chloro-6-pyridazinyloxy)ethylamino]-2-propanol obtained in (a) above, 20 ml of hydrazine hydrate and 20 ml of ethanol was refluxed overnight with stirring. The solvent was removed under reduced pressure. A solution of the residue in 100 ml of benzene was extracted with 30 ml of 10% hydrochloric acid. The aqueous layer was made alkaline with 10% sodium hydroxide and extracted with chloroform, and the organic layer was dried over magnesium sulfate. The solvent was evaporated. To a solution of the residue in 20 ml of ethanol was added 57 ml of 1N hydrochloric acid, and the solvent was evaporated below 40° C. under reduced pressure. A solution of the residue in ethanol was stored at 0° C. overnight. Recrystallization of the product from methanol-ethanol gave 1.21 g of 1-(2-chloro-5-methylphenoxy)-3-[1,1-dimethyl-2-(3-hydrazino-6-pyridazinyloxy)ethylamino]-2-propanol hydrochloride as pale yellow pillar-like crystals having a melting point of 204.6° to 205.7° C.

NMR(D$_2$O) δ: 1.52, 1.55 (6H, double s), 2.29 (3H, s), 3.30–3.52 (2H, m), 4.05–4.30 (3H, m), 4.40 (2H, s), 6.79 (1H, d, J=6 Hz), 6.87 (1H, s), 7.21 (1H, d, J=6 Hz), 7.17 (2H, s).

EXAMPLE 4

(a) A mixture of 4.83 g of 3-(2-amino-2-methylpropoxy)-6-chloropyridazine obtained in Example 1(a), 5.0 g of 1-[2-(2-methoxyethyl)phenoxy]-2,3-epoxypropane and 200 ml of ethanol was refluxed for 4 hours, and the solvent was evaporated under reduced pressure. A solution of the residue in benzene was extracted with 1N hydrochloric acid. The aqueous layer was extracted with chloroform, washed successively with 5% sodium carbonate and water, and the organic layer was dried over magnesium sulfate. The solvent was evaporated to give 3.8 g of 1-[2-(2-methoxyethyl)phenoxy]-3-[1,1-dimethyl-2-(3-chloro-6-pyridazinyloxy)ethylamino]-2-propanol.

NMR(CDCl$_3$) δ: 1.21 (6H, s), 2.30–2.70 (2H, m), 2.70–3.05 (4H, m), 3.30 (3H, s), 3.57 (2H, t, J=6 Hz), 4.00 (3H, broad s), 4.33 (2H, s), 6.70–7.24 (4H, m), 6.93 (1H, d, J=9 Hz), 7.32 (1H, d, J=9 Hz).

(b) A mixture of 1.8 g of 1-[2-(2-methoxyethyl)phenoxy]-3-[1,1-dimethyl-2-(3-chloro-6-pyridazinyloxy)ethylamino]-2-propanol obtained in (a) above, 15 ml of hydrazine hydrate and 30 ml of ethanol was refluxed overnight with stirring. The solvent was removed under reduced pressure. A solution of the residue in 90 ml of acetone was refluxed for 15 minutes. After evaporating the solvent, a solution of the oily residue in chloroform was washed successively with 5% sodium carbonate and an aqueous solution of sodium chloride and dried over magnesium sulfate. The solvent was evaporated and the crude product was purified by thin-layer chromatography [silica gel (Merck GF$_{254}$); chloroform/methanol=9/1] to give 219 mg of 1-[2-(2-methoxyethyl)phenoxy]-3-[1,1-dimethyl-2-(3-isopropylidenehydrazino-6-pyridazinyloxy)ethylamino]-2-propanol as a pale yellow oil.

NMR(CD$_3$OD) δ: 1.25 (6H, s), 1.94, 2.00 (6H, double s), 2.50–3.10 (4H, m), 3.29 (3H, s), 3.52 (2H, t, J=6 Hz), 3.98 (3H, s), 4.20 (2H, s), 6.98 (1H, d, J=9 Hz), 7.46 (1H, d, J=9 Hz), 6.66–7.30 (4H, m).

(c) A mixture of 2.0 g of 1-[2-(2-methoxyethyl)phenoxy]-3-[1,1-dimethyl-2-(3-chloro-6-pyridazinyloxy)ethylamino]-2-propanol obtained in (a) above, 20 ml of hydrazine hydrate and 40 ml of ethanol was refluxed overnight. After removing the solvent under reduced pressure, a solution of the residue in chloroform was washed with water, dried over magnesium sulfate, and concentrated to dryness. To a solution of the residue in ethanol was added hydrogen chloride ether solution. The solvent was evaporated under reduced pressure. A solution of the crude product in 2 ml of ethanol was added dropwise to 20 ml of ether. The resulting precipitate was separated by decantation to give 1.0 g of 1-[2-(2-methoxyethyl)phenoxy]-3-[1,1-dimethyl-2-(3-hydrazino-6-pyridazinyloxy)ethylamino]-2-propanol hydrochloride having a melting point of 173.3° to 174.1° C.

NMR(D$_2$O) δ: 1.58 (6H, s), 2.82 (2H, t, J=6 Hz), 3.23–3.49 (2H, m), 3.33 (3H, s), 3.65 (2H, t, J=7 Hz), 3.99–4.35 (3H, m), 4.42 (2H, s), 6.80–7.45 (4H, m), 7.28 (2H, s).

In the same way as in Example 2, 3-(2-amino-2-methylpropoxy)-6-chloropyridazine was reacted with the corresponding epoxide and then the product was converted to the corresponding hydrazine or hydrazone compound. Thus, the compounds shown in Examples 5 to 54 below were obtained.

EXAMPLE 5

(a) 1-(2-Chlorophenoxy)-3-[1,1-dimethyl-2-(3-chloro-6-pyridazinyloxy)ethylamino]-2-propanol.

NMR(CDCl$_3$) δ: 1.21 (6H, s), 2.50–3.04 (4H, m), 4.00 (3H, broad s), 4.33 (2H, s), 6.70–7.45 (4H, m), 6.90 (1H, d, J=9 Hz), 7.31 (1H, d, J=9 Hz).

(b) 1-(2-Chlorophenoxy)-3-[1,1-dimethyl-2-(3-isopropylidenehydrazino-6-pyridazinyloxy)ethylamino]-2-propanol.

NMR(CD$_3$OD) δ: 1.22 (6H, s), 1.94 (3H, s), 2.01 (3H, s), 2.74–2.99 (2H, m), 4.04 (3H, broad s), 4.19 (2H, s), 6.70–7.32 (4H, m), 6.95 (1H, d, J=9 Hz), 7.45 (1H, d, J=9 Hz).

(c) 1-(2-Chlorophenoxy)-3-[1,1-dimethyl-2-(3-hydrazino-6-pyridazinyloxy)ethylamino]-2-propanol hydrochloride.

NMR(D$_2$O) δ: 1.60 (6H, s), 3.31–3.59 (2H, m), 4.15–4.50 (3H, m), 4.46 (2H, s), 6.89–7.56 (4H, m), 7.24 (2H, s).

EXAMPLE 6

(a) 1-(2-Methylphenoxy)-3-[1,1-dimethyl-2-(3-chloro-6-pyridazinyloxy)ethylamino]-2-propanol.

NMR(CDCl$_3$) δ: 1.22 (6H, s), 2.18 (3H, s), 2.40–2.70 (2H, broad s), 2.71–2.95 (2H, m), 3.97 (3H, broad s), 4.32 (2H, s), 6.62–7.20 (4H, m), 6.87 (1H, d, J=9 Hz), 7.31 (1H, d, J=9 Hz).

(b) 1-(2-Methylphenoxy)-3-[1,1-dimethyl-2-(3-isopropylidenehydrazino-6-pyridazinyloxy)ethylamino]-2-propanol.

NMR(CDCl$_3$) δ: 1.21 (6H, s), 1.91 (3H, s), 2.01 (3H, s), 2.18 (3H, s), 2.70–2.98 (2H, m), 3.10–4.50 (2H, broad s), 3.97 (3H, broad s), 4.22 (2H, s), 6.63–7.20 (4H, m), 6.84 (1H, d, J=9 Hz), 7.49 (1H, d, J=9 Hz).

(c) 1-(2-Methylphenoxy)-3-[1,1-dimethyl-2-(3-hydrazino-6-pyridazinyloxy)ethylamino]-2-propanol hydrochloride.

NMR(D$_2$O) δ: 1.57 (6H, s), 2.12 (3H, s), 3.20–3.53 (2H, m), 4.03–4.57 (3H, m), 4.41 (2H, s), 6.72–7.30 (4H, m), 7.17 (2H, s).

(d) A mixture of 200 mg of 1-(2-methylphenoxy)-3-[1,1-dimethyl-2-(3-hydrazino-6-pyridazinyloxy)ethylamino]-2-propanol hydrochloride obtained in (c) above, 2 ml of acetone and 2 ml of methanol was refluxed for 6 hours. The solvent was evaporated under reduced pressure. The resulting crude product was crystallized from a mixture of ethanol and acetone to give 194 mg of 1-(2-methylphenoxy)-3-[1,1-dimethyl-2-(3-isopropylidenehydrazino-6-pyridazinyloxy)ethylamino]-2-propanol hydrochloride having a melting point of 164.5° to 169.0° C.

NMR(CD$_3$OD) δ: 1.57 (6H, s), 2.16 (6H, s), 2.18 (3H, s), 3.18–3.49 (2H, m), 3.90–4.60 (3H, m), 4.45 (2H, s), 6.70–7.27 (4H, m), 7.51 (1H, d, J=9 Hz), 7.75 (1H, d, J=9 Hz).

EXAMPLE 7

(a) 1-(2-Bromophenoxy)-3-[1,1-dimethyl-2-(3-chloro-6-pyridazinyloxy)ethylamino]-2-propanol.

NMR(CDCl$_3$) δ: 1.20 (6H, s), 2.65 (2H, broad s), 2.75–2.98 (2H, m), 3.98 (3H, broad s), 4.32 (2H, s), 6.65–7.68 (4H, m), 6.91 (1H, d, J=9 Hz), 7.31 (1H, d, J=9 Hz).

(b) 1-(2-Bromophenoxy)-3-[1,1-dimethyl-2-(3-isopropylidenehydrazino-6-pyridazinyloxy)ethylamino]-2-propanol.

Melting point: 132.5°–134.5° C.

NMR(CDCl$_3$) δ: 1.21 (6H, s), 1.92 (3H, s), 2.02 (3H, s), 2.48–3.25 (2H, m), 2.78–3.05 (2H, m), 4.00 (3H, broad s), 4.23 (2H, s), 6.65–7.68 (4H, m), 6.88 (1H, d, J=9 Hz), 7.50 (1H, d, J=9 Hz).

(c) 1-(2-Bromophenoxy)-3-[1,1-dimethyl-2-(3-hydrazino-6-pyridazinyloxy)ethylamino]-2-propanol hydrochloride.

Melting point: 181.0°–184.5° C.

NMR(D$_2$O) δ: 1.60 (6H, s), 3.35–3.65 (2H, m), 4.02–4.40 (3H, m), 4.45 (2H, s), 6.82–7.72 (4H, m), 7.23 (2H, s).

EXAMPLE 8

(a) 1-(2-Ethylphenoxy)-3-[1,1-dimethyl-2-(3-chloro-6-pyridazinyloxy)ethylamino]-2-propanol.

NMR(CDCl$_3$) δ: 1.15 (3H, t, J=7 Hz), 1.22 (6H, s), 2.50–3.20 (2H, m) 2.60 (2H, q, J=7 Hz), 2.70–3.10 (2H, m), 3.98 (3H, broad s), 4.32 (2H, s), 6.66–7.35 (4H, m), 6.88 (1H, d, J=9 Hz), 7.29 (1H, d, J=9 Hz).

(b) 1-(2-Ethylphenoxy)-3-[1,1-dimethyl-2-(3-isopropylidenehydrazino-6-pyridazinyloxy)ethylaminol]-2-propanol.

NMR(CDCl₃) δ: 1.14 (3H, t, J=7 Hz), 1.21 (6H, s), 1.90 (3H, s), 2.01 (3H, s), 2.51–3.15 (2H, m), 2.60 (2H, q, J=7 Hz), 2.70–3.10 (2H, m), 3.98 (3H, broad s), 4.22 (2H, s), 6.60–7.32 (4H, m), 6.84 (1H, d, J=9 Hz), 7.49 (1H, d, J=9 Hz).

(c) 1-(2-Ethylphenoxy)-3-[1,1-dimethyl-2-(3-hydrazino-6-pyridazinyloxy)ethylamino]-2-propanol hydrochloride.

NMR(D₂) δ: 1.10 (3H, t, J=7 Hz), 1.57 L (6H, s), 2.52 (2H, q, J=7 Hz), 3.25–3.51 (2H, m), 4.00–4.55 (3H, m), 4.41 (2H, s), 6.75–7.41 (4H, m), 7.20 (2H, s).

EXAMPLE 9

(a) 1-(2-Propylphenoxy)-3-[1,1-dimethyl-2-(3-chloro-6-pyridazinyloxy)ethylamino]-2-propanol.

NMR(CDCl₃) δ: 0.89 (3H, t, J=7 Hz), 1.10–1.93 (2H, m), 1.23 (6H, s), 2.56 (2H, t, J=7 Hz), 2.66 (2H, broad s), 2.70–3.10 (2H, m), 3.97 (3H, broad s), 4.33 (2H, s), 6.65–7.35 (4H, m), 6.91 (1H, d, J=9 Hz), 7.32 (1H, d, J=9 Hz).

(b) 1-(2-Propylphenoxy)-3-[1,1-dimethyl-2-(3-isopropylidenehydrazino-6-pyridazinyloxy)ethylamino]-2-propanol.

NMR(CDCl₃) δ: 0.88 (3H, t, J=7 Hz), 1.10–1.82 (2H, m), 1.20 (6H, s), 1.90 (3H, s), 2.01 (3H, s) 2.56 (2H, t, J=8 Hz), 2.70–3.35 (2H, m), 2.73–3.10 (2H, m), 3.97 (3H, broad s), 4.23 (2H, s), 6.65–7.35 (4H, m), 6.84 (1H, d, J=9 Hz), 7.49 (1H, d, J=9 Hz).

(c) 1-(2-Propylphenoxy)-3-[1,1-dimethyl-2-(3-hydrazino-6-pyridazinyloxy)ethylamino]-2-propanol hydrochloride.

Melting point: 188.0°–189.5° C.

NMR(D₂O) δ: 0.86 (3H, t, J=7 Hz), 1.10–2.00 (2H, m), 1.56 (6H, s), 2.50 (2H, t, J=7 Hz), 3.19–3.51 (2H, m), 4.01–4.35 (3H, m), 4.40 (2H, s), 6.73–7.46 (4H, m), 7.22 (2H, s).

EXAMPLE 10

(a) 1-(2-Allylphenoxy)-3-[1,1-dimethyl-2-(3-chloro-6-pyridazinyloxy)ethylamino]-2-propanol.

NMR(CDCl₃) δ: 1.21 (6H, s), 2.52 (2H, broad s), 2.70–2.92 (2H, m), 3.34 (2H, d, J=6 Hz), 3.97 (3H, broad s), 4.32 (2H, s), 4.77–4.96 (1H, m), 5.09 (1H, broad s), 5.60–6.30 (1H, m), 6.68–7.35 (4H, m), 6.92 (1H, d, J=9 Hz), 7.31 (1H, d, J=9 Hz).

(b) 1-(2-Allylphenoxy)-3-[1,1-dimethyl-2-(3-isopropylidenehydrazino-6-pyridazinyloxy)ethylamino]-2-propanol.

NMR(CDCl₃) δ: 1.19 (6H, s), 1.91 (3H, s), 2.01 (3H, s), 2.47–3.70 (2H, m), 2.70–2.92 (2H, m), 3.34 (2H, d, J=6 Hz), 3.96 (3H, broad s), 4.21 (2H, s), 4.72–4.98 (1H, m), 5.08 (1H, broad s), 5.60–6.30 (1H, m), 6.67–7.29 (4H, m), 6.86 (1H, d, J=9 Hz), 7.49 (1H, d, J=9 Hz).

(c) 1-(2-Allylphenoxy)-3-[1,1-dimethyl-2-(3-hydrazino-6-pyridazinyloxy)ethylamino]-2-propanol.

Melting point: 173.5°–177.1° C.

NMR(D₂O) δ: 1.60 (6H, s), 3.18–3.50 (4H, m), 4.14 (2H, d, J=5 Hz), 4.43 (3H, broad s), 4.80–5.08 (1H, m), 5.15 (1H, broad s), 5.60–6.30 (1H, m), 6.80–7.38 (4H, m), 7.29 (2H, s).

EXAMPLE 11

(a) 1-(2-Trifluoromethylphenoxy)-3-[1,1-dimethyl-2-(3-chloro-6-pyridazinyloxy)ethylamino]-2-propanol.

NMR(CDCl₃) δ: 1.20 (6H, s), 2.70 (2H, broad s), 2.78–2.96 (2H, m), 4.02 (3H, broad s), 4.31 (2H, s), 6.92 (1H, d, J=9 Hz), 6.82–7.15 (2H, m), 7.31 (1H, d, J=9 Hz), 7.30–7.63 (2H, m).

(b) 1-(2-Trifluoromethylphenoxy)-3-[1,1-dimethyl-2-(3-isopropylidenehydrazino-6-pyridazinyloxy)ethylamino]-2-propanol.

Melting point: 127°–130° C.

NMR(CDCl₃) δ: 1.20 (6H, s), 1.91 (3H, s), 2.01 (3H, s), 2.78–2.97 (2H, m), 3.00–4.00 (2H, m), 4.04 (3H, broad s), 4.22 (2H, s), 6.87 (1H, d, J=9 Hz), 6.79–7.15 (2H, m), 7.23–7.66 (2H, m). 7.49 (1H, d, J=9 Hz).

(c) 1-(2-Trifluoromethylphenoxy)-3-[1,1-dimethyl-2-(3-hydrazino-6-pyridazinyloxy)ethylamino]-2-propanol hydrochloride.

Melting point: 194°–196° C.

NMR(D₂O) δ: 1.57 (6H, s), 3.20–3.45 (2H, m), 4.15–4.55 (3H, m), 4.41 (2H, s), 6.95–7.30 (2H, m), 7.34 (2H, s), 7.45–7.80 (2H, m).

EXAMPLE 12

(a) 1-[2-(2-Hydroxyethyl)phenoxy]-3-[1,1-dimethyl-2-(3-chloro-6-pyridazinyloxy)ethylamino]-2-propanol.

NMR(CDCl₃) δ: 1.22 (6H, s), 2.50–3.28 (4H, m), 3.11 (2H, s), 3.43 (1H, s), 3.77 (2H, t, J=7 Hz), 3.98 (3H, broad s), 4.32 (2H, s), 6.63–7.37 (4H, m), 6.95 (1H, d, J=9 Hz), 7.32 (1H, d, J=9 Hz).

(b) 1-[2-(2-Hydroxyethyl)phenoxy]-3-[1,1-dimethyl-2-(3-isopropylidenehydrazino-6-pyridazinyloxy)ethylamino]-2-propanol.

NMR(CDCl₃) δ: 1.21 (6H, s), 1.90 (3H, s), 2.01 (3H, s), 2.43–3.24 (3H, m), 2.55–3.15 (4H, m), 3.78 (2H, t, J=7 Hz), 3.97 (3H, broad s), 4.26 (2H, s), 6.67–7.37 (4H, m), 6.90 (1H, d, J=9 Hz), 7.50 (1H, d, J=9 Hz).

EXAMPLE 13

(a) 1-(2-Methoxymethylphenoxy)-3-[1,1-dimethyl-2-(3-chloro-6-pyridazinyloxy)ethylamino]-2-propanol.

NMR(CDCl₃) δ: 1.20 (6H, s), 2.67–2.90 (2H, m), 2.95 (2H, s), 3.33 (3H, s), 3.98 (3H, broad s), 4.31 (2H, s), 4.43 (2H, s), 6.70–7.40 (4H, m), 6.90 (1H, d, J=9 Hz), 7.30 (1H, d, J=9 Hz).

(b) 1-(2-Methoxymethylphenoxy)-3-[1,1-dimethyl-2-(3-hydrazino-6-pyridazinyloxy)ethylamino]-2-propanol hydrochloride.

Melting point: 175.3°–179.7° C.

NMR(D₂O) δ: 1.56 (6H, s), 3.24–3.52 (2H, m), 3.36 (3H, s), 4.05–4.60 (3H, m), 4.43 (2H, s), 4.45 (2H, s), 6.88–7.58 (4H, m), 7.30 (3H, s).

EXAMPLE 14

(a) 1-[2-(4-Methoxybutyl)phenoxy]-3-[1,1-dimethyl-2-(3-chloro-6-pyridazinyloxy)ethylamino]-2-propanol.

NMR(CDCl₃) δ: 1.21 (6H, s), 1.35–2.00 (4H, m), 2.30–3.15 (4H, m), 2.87 (2H, broad s), 3.15–3.56 (2H, m), 3.29 (3H, s), 3.97 (3H, broad s), 4.32 (2H, s), 6.60–7.35 (4H, m), 6.89 (1H, d, J=9 Hz), 7.30 (1H, d, J=9 Hz).

(b) 1-[2-(4-Methoxybutyl)phenoxy]-3-[1,1-dimethyl-2-(3-isopropylidenehydrazino-6-pyridazinyloxy)ethylamino]-2-propanol.

NMR(CDCl$_3$) δ: 1.28 (6H, s), 1.40–1.85 (4H, m), 1.92 (3H, s), 2.02 (3H, s), 2.35–3.19 (4H, m), 3.20–3.83 (4H, m), 3.29 (3H, s), 3.99 (3H, broad s), 4.29 (2H, s), 6.65–7.40 (4H, m), 6.95 (1H, d, J=9 Hz), 7.51 (1H, d, J=9 Hz).

EXAMPLE 15

(a) 1-(2-Ethoxymethylphenoxy)-3-[1,1-dimethyl-2-(3-chloro-6-pyridazinyloxy)ethylamino]-2-propanol.

NMR(CDCl$_3$) δ: 1.19 (3H, t, J=7 Hz), 1.20 (6H, s), 2.50–3.00 (4H, m), 3.50 (2H, q, J=7 Hz), 4.00 (3H, broad s), 4.32 (2H, s), 4.48 (2H, s), 6.70–7.43 (4H, m), 6.91 (1H, d, J=9 Hz), 7.31 (1H, d, J=9 Hz).

(b) 1-(2-Ethoxymethylphenoxy)-3-[1,1-dimethyl-2-(3-hydrazino-6-pyridazinyloxy)ethylamino]-2-propanol hydrochloride.

NMR(D$_2$O) δ: 1.20 (3H, t, J=7 Hz), 1.57 (6H, s), 3.12–3.52 (2H, m), 3.60 (2H, q, J=7 Hz), 3.99–4.32 (3H, m), 4.43 (2H, s), 4.49 (2H, s), 6.86–7.64 (4H, m), 7.32 (2H, s).

EXAMPLE 16

(a) 1-[2-(2-Ethylthioethyl)phenoxy]-3-[1,1-dimethyl-2-(3-chloro-6-pyridazinyloxy)ethylamino]-2-propanol.

NMR(CDCl$_3$) δ: 1.23 (3H, t, J=7 Hz), 1.23 (6H, s), 2.55 (2H, q, J=7 Hz), 2.56–2.72 (2H, m), 2.67–3.13 (6H, m), 3.98 (3H, s), 4.32 (2H, s), 6.67–7.23 (4H, m), 6.92 (1H, d, J=9 Hz), 7.32 (1H, d, J=9 Hz).

(b) 1-[2-(2-Ethylthioethyl)phenoxy]-3-[1,1-dimethyl-2-(3-isopropylidenehydrazino-6-pyridazinyloxy)ethylamino]-2-propanol.

NMR(CD$_3$OD) δ: 1.18 (3H, t, J=7 Hz), 1.22 (6H, s), 1.92 (3H, s), 1.98 (3H, s), 2.48 (2H, q, J=7 Hz), 2.54–3.10 (6H, m), 3.98 (3H, broad s), 4.18 (2H, s), 6.62–7.30 (4H, m), 6.98 (1H, d, J=9 Hz), 7.45 (1H, d, J=9 Hz).

(c) 1-[2-(2-Ethylthioethyl)phenoxy]-3-[1,1-dimethyl-2-(3-hydrazino-6-pyridazinyloxy)ethylamino]-2-propanol hydrochloride.

Melting point: 181.6°–182.5° C.

NMR(CD$_3$OD) δ: 1.18 (3H, t, J=7 Hz), 1.55 (6H, s), 2.49 (2H, q, J=7 Hz), 2.52–3.07 (6H, m), 3.90–4.40 (4H, m), 4.42 (2H, s), 6.66–7.33 (4H, m), 7.43 (2H, s).

EXAMPLE 17

(a) 1-[2-(2-acetylaminoethyl)phenoxy]-3-[1,1-dimethyl-2-(3-chloro-6-pyridazinyloxy)ethylamino]-2-propanol.

NMR(CDCl$_3$) δ: 1.20 (6H, s), 1.93 (3H, s), 2.60–3.18 (4H, m), 2.80 (2H, broad s), 3.18–3.69 (2H, m), 4.00 (3H, broad s), 4.34 (2H, s), 5.98–6.40 (1H, m), 6.69–7.38 (4H, m), 6.97 (1H, d, J=9 Hz), 7.35 (1H, d, J=9 Hz).

(b) 1-[2-(2-Acetylaminoethyl)phenoxy]-3-[1,1-dimethyl-2-(3-isopropylidenehydrazino-6-pyridazinyloxy)ethylamino]-2-propanol.

NMR(CD$_3$OD) δ: 1.25 (6H, s), 1.88 (3H, s), 1.95 (3H, s), 2.02 (3H, s), 2.60–3.04 (2H, m), 3.28–3.42 (2H, m), 4.00 (3H, broad s), 4.20 (2H, s), 6.68–7.26 (4H, m), 6.99 (1H, d, J=9 Hz), 7.48 (1H, d, J=9 Hz).

(c) 1-[2-(2-Acetylaminoethyl)phenoxy]-3-[1,1-dimethyl-2-(3-hydrazino-6-pyridazinyloxy)ethylamino]-2-propanol hydrochloride.

NMR(CD$_3$OD) δ: 1.56 (6H, s), 2.08 (3H, s), 2.80 (2H, t, J=8 Hz), 3.18–3.61 (4H, m), 3.96–4.22 (3H, m), 4.44 (2H, s), 6.80–7.30 (4H, m), 7.45 (2H, s).

EXAMPLE 18

(a) 1-[2-(2-Tetrahydrofurfuryloxyethyl)phenoxy]-3-[1,1-dimethyl-2-(3-chloro-6-pyridazinyloxy)ethylamino]-2-propanol.

NMR(CDCl$_3$) δ: 1.20 (6H, s), 1.38–2.20 (4H, m), 2.66 (2H, broad s), 2.68–3.10 (4H, m), 3.49 (2H, d, J=5 Hz), 3.60–4.23 (3H, m), 3.77 (2H, t, J=7 Hz), 3.97 (3H, broad s), 4.32 (2H, s), 6.65–7.35 (4H, m), 6.93 (1H, d, J=9 Hz), 7.32 (1H, d, J=9 Hz).

(b) 1-[2-(2-Tetrahydrofurfuryloxyethyl)phenoxy]-3-[1,1-dimethyl-2-(3-isopropylidenehydrazino-6-pyridazinyloxy)ethylamino]-2-propanol.

NMR(CDCl$_3$) δ: 1.20 (6H, s), 1.45–2.15 (4H, m), 1.91 (3H, s), 2.02 (3H, s), 2.45–3.20 (2H, m), 2.60–3.14 (4H, m), 3.41 (2H, d, J=5 Hz), 3.52–4.17 (3H, m), 3.57 (2H, t, J=7 Hz), 3.97 (3H, broad s), 4.23 (2H, s), 6.60–7.45 (4H, m), 6.89 (1H, d, J=9 Hz), 7.50 (1H, d, J=9 Hz).

(c) 1-[2-(2-Tetrahydrofurfuryloxyethyl)phenoxy]-3-[1,1-dimethyl-2-(3-hydrazino-6-pyridazinyloxy)ethylamino]-2-propanol hydrochloride.

Melting point: 168.0°–171.0° C.

NMR(D$_2$O) δ: 1.40–2.20 (4H, m), 1.56 (6H, s), 2.82 (2H, t, J=7 Hz), 3.20–4.01 (9H, m), 4.01–4.40 (3H, m), 4.42 (2H, s), 6.65–7.55 (4H, m), 7.24 (2H, s).

EXAMPLE 19

(a) 1-[2-(2-Allyloxyethyl)phenoxy]-3-[1,1-dimethyl-2-(3-chloro-6-pyridazinyloxy)ethylamino]-2-propanol.

NMR(CDCl$_3$) δ: 1.21 (6H, s), 2.20–2.75 (2H, m), 2.72–3.17 (4H, m), 3.62 (2H, t, J=6 Hz), 3.85–4.25 (2H, m), 3.98 (3H, broad s), 4.33 (2H, s), 4.95–5.40 (2H, m), 5.45–6.40 (1H, m), 6.70–7.37 (4H, m), 6.92 (1H, s, J=9 Hz), 7.32 (1H, m, J=9 Hz).

(b) 1-[2-(2-Allyloxyethyl)phenoxy]-3-[1,1-dimethyl-2-(3-isopropylidenehydrazino-6-pyridazinyloxy)ethylamino]-2-propanol.

NMR(CDCl$_3$) δ: 1.20 (6H, s), 1.91 (3H, s), 2.02 (3H, s), 2.50–3.15 (2H, m), 2.72–3.10 (4H, m), 3.62 (2H, t, J=6 Hz), 3.80–4.18 (2H, m), 3.99 (3H, broad s), 4.23 (2H, s), 4.95–5.41 (2H, m), 5.55–6.30 (1H, m), 6.69–7.40 (4H, m), 6.88 (1H, d, J=9 Hz), 7.50 (1H, d, 9 Hz).

EXAMPLE 20

(a) 1-(2-Ethynylphenoxy)-3-[1,1-dimethyl-2-(3-chloro-6-pyridazinyloxy)ethylamino]-2-propanol.

NMR(CDCl$_3$) δ: 1.22 (6H, s), 2.61–2.97 (2H, m), 2.28 (2H, s), 3.23 (1H, s), 4.02 (3H, broad s), 4.32 (2H, s), 6.72–7.52 (4H, m), 6.91 (1H, d, J=9 Hz), 7.31 (1H, d, J=9 Hz).

(b) 1-(2-Ethynylphenoxy)-3-[1,1-dimethyl-2-(3-hydrazino-6-pyridazinyloxy)ethylamino]-2-propanol hydrochloride.

Melting point: 188.1°–188.5° C.

NMR(CD₃OD) δ: 1.55 (6H, s), 3.20–3.47 (2H, m), 3.64 (1H, s), 3.90–4.38 (3H, m), 4.42 (2H, s), 6.85–7.52 (4H, m), 7.37 (2H, s).

EXAMPLE 21

(a) 1-Phenoxy-3-[1,1-dimethyl-2-(3-chloro-6-pyridazinyloxy)ethylamino]-2-propanol.

NMR(CDCl₃) δ: 1.20 (6H, s), 2.51 (2H, broad s), 2.65–3.06 (2H, m), 3.95 (3H, broad s), 4.32 (2H, s), 6.72–7.50 (5H, m), 6.90 (1H, d, J=9 Hz), 7.31 (1H, d, J=9 Hz).

(b) 1-Phenoxy-3-[1,1-dimethyl-2-(3-hydrazino-6-pyridazinyloxy)ethylamino]-2-propanol hydrochloride.

NMR(D₂O) δ: 1.56 (6H, s), 3.22–3.50 (2H, m), 3.97–4.31 (3H, m), 4.43 (2H, s), 6.78–7.50 (5H, m), 7.29 (2H, s).

EXAMPLE 22

1-(2-Hydroxyphenoxy)-3-[1,1-dimethyl-2-(3-isopropylidenehydrazino-6-pyridazinyloxy)ethylamino]-2-propanol.

NMR(CDCl₃) δ: 1.17 (6H, s), 1.89 (3H, s), 2.00 (3H, s), 2.68–3.02 (2H, m), 4.00 (3H, broad s), 4.23 (2H, s), 4.94–6.03 (3H, m), 6.83 (4H, broad s), 6.87 (1H, d, J=9 Hz), 7.50 (1H, d, J=9 Hz).

EXAMPLE 23

(a) 1-(2-Ethoxyphenoxy)-3-[1,1-dimethyl-2-(3-chloro-6-pyridazinyloxy)ethylamino]-2-propanol.

NMR(CDCl₃) δ: 1.20 (6H, s), 1.38 (3H, t, J=7 Hz), 2.62–2.78 (2H, m), 2.68 (2H, broad s), 3.98 (3H, broad s), 4.04 (2H, q, J=7 Hz), 4.32 (2H, s), 6.88 (4H, s), 6.91 (1H, d, J=9 Hz), 7.31 (1H, d, J=9 Hz).

(b) 1-(2-Ethoxyphenoxy)-3-[1,1-dimethyl-2-(3-hydrazino-6-pyridazinyloxy)ethylamino]-2-propanol hydrochloride.

NMR(CD₃OD) δ: 1.38 (3H, t, J=7 Hz), 1.57 (6H, s), 3.23–3.55 (2H, m), 4.07 (2H, q, J=7 Hz), 3.98–4.40 (3H, m), 4.42 (2H, s), 6.92 (4H, s), 7.38 (2H, s).

EXAMPLE 24

(a) 1-(2-Benzyloxyphenoxy)-3-[1,1-dimethyl-2-(3-chloro-6-pyridazinyloxy)ethylamino]-2-propanol.

NMR(CDCl₃) δ: 1.15 (6H, s), 2.50–3.10 (2H, m), 2.80 (2H, broad s), 4.00 (3H, broad s), 4.28 (2H, s), 5.06 (2H, s), 6.87 (1H, d, J=9 Hz), 6.90 (4H, s), 7.32 (1H, d, J=9 Hz), 7.34 (5H, broad s).

(b) 1-(2-Benzyloxyphenoxy)-3-[1,1-dimethyl-2-(3-isopropylidenehydrazino-6-pyridazinyloxy)ethylamino]-2-propanol.

NMR(CDCl₃) δ: 1.16 (6H, s), 1.90 (3H, s), 2.01 (3H, s), 2.50–3.55 (2H, m), 2.69–2.91 (2H, m), 4.01 (3H, broad s), 4.20 (2H, s), 5.06 (2H, s), 6.83 (1H, d, J=9 Hz), 6.90 (4H, s), 7.35 (5H, broad s), 7.47 (1H, d, J=9 Hz).

(c) 1-(2-Benzyloxyphenoxy)-3-[1,1-dimethyl-2-(3-hydrazino-6-pyridazinyloxy)ethylamino]-2-propanol hydrochloride.

Melting point: 174°–176° C.

NMR(D₂O) δ: 1.43 (6H, s), 3.23–3.50 (2H, m), 4.04–4.28 (3H, m), 4.32 (2H, s), 5.09 (2H, s), 7.03 (4H, s), 7.17 (2H, s), 7.44 (5H, s).

EXAMPLE 25

1-(2-Furfuryloxyphenoxy)-3-[1,1-dimethyl-2-(3-isopropylidenehydrazino-6-pyridazinyloxy)ethylamino]-2-propanol.

NMR(CDCl₃) δ: 1.17 (6H, s), 1.90 (3H, s), 2.01 (3H, s), 2.53–3.31 (2H, m), 2.70–2.91 (2H, m), 3.99 (3H, broad s), 4.20 (2H, s), 4.98 (2H, s), 6.20–6.47 (2H, m), 6.85 (1H, d, J=9 Hz), 6.92 (4H, s), 7.30–7.56 (1H, m), 7.47 (1H, d, J=9 Hz).

EXAMPLE 26

(a) 1-(2-Methoxymethoxyphenoxy)-3-[1,1-dimethyl-2-(3-chloro-6-pyridazinyloxy)ethylamino]-2-propanol.

NMR(CDCl₃) δ: 1.21 (6H, s), 2.29–2.95 (2H, m), 2.50–4.00 (2H, m), 2.99 (2H, broad s), 3.47 (3H, s), 4.00 (3H, broad s), 4.32 (2H, s), 5.13 (2H, s), 6.71–7.31 (4H, m), 6.92 (1H, d, J=9 Hz), 7.32 (1H, d, J=9 Hz).

(b) 1-(2-Methoxymethoxyphenoxy)-3-[1,1-dimethyl-2-(3-isopropylidenehydrazino-6-pyridazinyloxy)ethylamino]-2-propanol.

NMR(CDCl₃) δ: 1.20 (6H, s), 1.91 (3H, s), 2.01 (3H, s), 2.50–4.00 (2H, m), 2.70–3.10 (2H, m), 3.47 (3H, s), 4.02 (3H, broad s), 4.22 (2H, s), 5.14 (2H, s), 6.71–7.45 (4H, m), 6.91 (1H, d, J=9 Hz), 7.50 (1H, d, J=9 Hz).

EXAMPLE 27

(a) 1-[2-(2-methoxyethoxy)phenoxy]-3-[1,1-dimethyl-2-(3-chloro-6-pyridazinyloxy)ethylamino]-2-propanol.

NMR(CDCl₃) δ: 1.19 (6H, s), 2.50–2.98 (2H, m), 2.64–2.85 (2H, m), 3.42 (3H, s), 3.60–3.90 (2H, m), 3.90–4.27 (5H, m), 4.31 (2H, s), 6.90 (4H, s), 6.92 (1H, d, J=9 Hz), 7.32 (1H, d, J=9 Hz).

(b) 1-[2-(2-Methoxyethoxy)phenoxy]-3-[1,1-dimethyl-2-(3-isopropylidenehydrazino-6-pyridazinyloxy)ethylamino]-2-propanol.

NMR(CD₃OD) δ: 1.23 (6H, s), 1.93 (3H, s), 2.00 (3H, s), 2.58–3.08 (2H, m), 3.38 (3H, s), 3.56–3.80 (2H, m), 3.85–4.12 (5H, m), 4.18 (2H, s), 6.89 (4H, s), 6.98 (1H, d, J=9 Hz), 7.44 (1H, d, J=9 Hz).

(c) 1-[2-(2-Methoxyethoxy)phenoxy]-3-[1,1-dimethyl-2-(3-hydrazino-6-pyridazinyloxy)ethylamino]-2-propanol hydrochloride.

NMR(D₂O) δ: 1.58 (6H, s), 3.38 (2H, s), 3.45 (3H, s), 3.20–3.45 (2H, m), 4.05–4.32 (5H, m), 4.43 (2H, s), 7.00 (4H, s), 7.22 (2H, s).

EXAMPLE 28

(a) 1-(2-Allyloxyphenoxy)-3-[1,1-dimethyl-2-(3-chloro-6-pyridazinyloxy)ethylamino]-2-propanol.

NMR(CDCl₃) δ: 1.20 (6H, s), 2.68–2.89 (2H, m), 2.72 (2H, broad s), 3.98 (3H, broad s), 4.30(2H, s), 4.42–4.65 (2H, m), 5.05–5.60 (2H, m), 5.61–6.40 (1H, m), 6.87 (4H, s), 6.90 (1H, d, J=9 Hz), 7.30 (1H, d, J=9 Hz).

(b) 1-(2-Allyloxyphenoxy)-3-[1,1-dimethyl-2-(3-hydrazino-6-pyridazinyloxy)ethylamino]-2-propanol hydrochloride.

Melting point: 164.8°–166.4° C.

NMR(D₂O) δ: 1.58 (6H, s), 3.27–3.57 (2H, m), 4.02–4.37 (3H, m), 4.43 (2H, s), 4.50–4.70 (2H, m), 5.20–5.69 (2H, m), 5.72–6.50 (1H, m), 7.00 (4H, s), 7.22 (2H, s).

EXAMPLE 29

(a) 1-(3-Chlorophenoxy)-3-[1,1-dimethyl-2-(3-chloro-6-pyrdidazinyloxy)ethylamino]-2-propanol.

NMR(CDCl$_3$) δ: 1.22 (6H, s), 2.48–3.10 (2H, m), 2.68–2.92 (2H, m), 3.95 (3H, broad s), 4.32 (2H, s), 6.62–7.38 (4H, m), 6.95 (1H, d, J=9 Hz), 7.35 (1H, d, J=9 Hz).

(b) 1-(3-Chlorophenoxy)-3-[1,1-dimethyl-2-(3-hydrazino-6-pyridazinyloxy)ethylamino]-2-propanol hydrochloride.

Melting point: 150.0°–155.0° C.

NMR(D$_2$O) δ: 1.60 (6H, s), 3.27–3.60 (2H, m), 4.02–4.40 (3H, m) 4.46 (2H, s), 6.76–7.50 (4H, m), 7.33 (2H, s).

EXAMPLE 30

(a) 1-(3-Bromophenoxy)-3-[1,1-dimethyl-2-(3-chloro-6-pyridazinyloxy)ethylamino]-2-propanol.

NMR(CDCl$_3$) δ: 1.20 (6H, s), 2.61 (2H, broad s), 2.60–2.91 (2H, m), 3.94 (3H, broad s), 4.32 (2H, s), 6.70–7.20 (4H, m), 6.92 (1H, d, J=9 Hz), 7.34 (1H, d, J=9 Hz).

(b) 1-(3-Bromophenoxy)-3-[1,1-dimethyl-2-(3-isopropylidenehydrazino-6-pyridazinyloxy)ethylamino]-2-propanol.

NMR(CDCl$_3$) δ: 1.22 (6H, s), 1.92 (3H, s), 2.02 (3H, s), 2.60–3.88 (2H, m), 2.70–2.95 (2H, m), 3.95 (3H, broad s), 4.22 (2H, s), 6.65–7.19 (4H, m), 6.89 (1H, d, J=9 Hz), 7.52 (1H, d, J=9 Hz).

(c) 1-(3-Bromophenoxy)-3-[1,1-dimethyl-2-(3-hydrazino-6-pyridazinyloxy)ethylamino]-2-propanol hydrochloride.

Melting point: 180.5°–183.0° C.

NMR(D$_2$O) δ: 1.55 (6H, s), 3.23–3.55 (2H, m), 3.95–4.37 (3H, m), 4.40 (2H, s), 6.70–7.45 (4H, m), 7.26 (2H, s).

EXAMPLE 31

(a) 1-(3-Fluorophenoxy)-3-[1,1-dimethyl-2-(3-chloro-6-pyrdidazinyloxy)ethylamino]-2--propanol.

NMR(CDCl$_3$) δ: 1.20 (6H, s), 2.59 (2H, broad s), 2.58–2.92 (2H, m), 3.95 (3H, broad s), 4.32 (2H, s), 6.45–7.32 (4H, m). 6.92 (1H, d, J=9 Hz), 7.32 (1H, d, J=9 Hz).

(b) 1-(3-Fluorophenoxy)-3-[1,1-dimethyl-2-(3-isopropylidenehydrazino-6-pyridazinyloxy)ethylamino]-2-propanol.

NMR(CDCl$_3$) δ: 1.20 (6H, s), 1.90 (3H, s), 2.01 (3H, s), 2.33–3.40 (4H, m), 3.94 (3H, broad s), 4.22 (2H, s), 6.42–7.30 (4H, m), 6.86 (1H, d, J=9 Hz), 7.48 (1H, d, J=9 Hz).

(c) 1-(3-Fluorophenoxy)-3-[1,1-dimethyl-2-(3-hydrazino-6-pyridazinyloxy)ethylamino]-2-propanol hydrochloride.

Melting point: 173°–176° C.

NMR(D$_2$O) δ: 1.55 (6H, s), 3.22–3.45 (2H, m), 4.01–4.55 (3H, m), 4.42 (2H, s), 6.50–7.45 (4H, m), 7.32 (2H, s).

EXAMPLE 32

(a) 1-(3-Methylphenoxy)-3-[1,1-dimethyl-2-(3-chloro-6-pyridazinyloxy)ethylamino]-2-propanol.

NMR(CDCl$_3$) δ: 1.21 (6H, s), 2.30 (3H, s), 2.68–2.89 (2H, m), 2.69 (2H, s), 3.94 (3H, broad s), 4.32 (2H, s), 6.52–7.21 (4H, m), 6.91 (1H, d, J=9 Hz), 7.31 (1H, d, J=9 Hz).

(b) 1-(3-Methylphenoxy)-3-[1,1-dimethyl-2-(3-hydrazino-6-pyridazinyloxy)ethylamino]-2-propanol hydrochloride.

Melting point: 168°–171° C.

NMR(D$_2$O) δ: 1.57 (6H, s), 2.30 (3H, s), 3.28–4.00 (2H, m) 4.05–4.55 (3H, m), 4.43 (2H, s), 6.60–7.25 (4H, m), 7.27 (2H, s).

EXAMPLE 33

(a) 1-(3-Ethylphenoxy)-3-[1,1-dimethyl-2-(3-chloro-6-pyridazinylixy)ethylamino]-2-propanol.

NMR(CDCl$_3$) δ: 1.19 (3H, t, J=7 Hz), 1.21 (6H, s), 2.55–3.10 (2H, m), 2.59 (2H, q, J=7 Hz), 2.65–3.95 (2H, m), 3.95 (3H, broad s), 4.32 (2H, s), 6.53–7.35 (4H, m), 6.89 (1H, d, J=9 Hz), 7.30 (1H, d, J=9 Hz).

(b) 1-(3-Ethylphenoxy)-3-[1,1-dimethyl-2-(3-hydrazino-6-pyridazinyloxy)ethylamino]-2-propanol hydrochloride.

Melting point: 171.5°–173.5° C.

NMR(D$_2$O) δ: 1.19 (3H, t, J=7 Hz), 1.58 (6H, s), 2.61 (2H, q, J=7 Hz), 3.20–3.53 (2H, m), 4.02–4.45 (3H, m), 4.43 (2H, s), 6.60–7.43 (4H, m), 7.28 (2H, s).

EXAMPLE 34

(a) 1-(3-Trifluoromethylphenoxy)-3-[1,1-dimethyl-2-(3-chloro-6-pyridazinyloxy)ethylamino]-2-propanol.

NMR(CDCl$_3$) δ: 1.21 (6H, s), 2.60 (2H, broad s), 2.68–2.93 (2H, m), 3.97 (3H, broad s), 4.33 (2H, s), 6.90–7.40 (4H, m), 6.92 (1H, d, J=9 Hz), 7.32 (1H, d, J=9 Hz).

(b) 1-(3-Trifluoromethylphenoxy)-3-[1,1-dimethyl-2-(3-isopropylidenehydrazino-6-pyridazinyloxy)ethylamino]-2-propanol.

NMR(CDCl$_3$) δ: 1.20 (6H, s), 1.92 (3H, s), 2.02 (3H, s), 2.50–3.86 (2H, m), 2.70–2.95 (2H, m), 4.00 (3H, broad s), 4.25 (2H, s), 6.88 (1H, d, J=9.5 Hz), 6.90–7.43 (4H, m), 7.52 (1H, d, J=9.5 Hz).

(c) 1-(3-Trifluoromethylphenoxy)-3-[1,1-dimethyl-2-(3-hydrazino-6-pyridazinyloxy)ethylamino]-2-propanol hydrochloride.

Melting point: 181.1°–183.4° C.

NMR(D$_2$O) δ: 1.58 (6H, s), 3.20–3.53 (2H, m), 4.10–4.53 (3H, m), 4.44 (2H, s), 7.05–7.45 (4H, m), 7.31 (2H, s).

EXAMPLE 35

(a) 1-[3-(2-Methoxyethyl)phenoxy]-3-[1,1-dimethyl-2-(3-chloro-6-pyridazinyloxy)ethylamino]-2-propanol.

NMR(CDCl$_3$) δ: 1.21 (6H, s), 2.50–3.12 (4H, m) 2.80 (2H, t, J=7 Hz), 3.32 (3H, s), 3.58 (2H, t, J=7 Hz), 3.95 (3H, broad s), 4.32 (2H, s), 6.56–6.95 (3H, m), 6.90 (2H, d, J=9 Hz), 7.01–7.36 (1H, m), 7.31 (2H, d, J=9 Hz).

(b) 1-[3-(2-Methoxyethyl)phenoxy]-3-[1,1-dimethyl-2-(3-hydrazino-6-pyridazinyloxy)ethylamino]-2-propanol hydrochloride.

NMR(D$_2$O) δ: 1.56 (6H, s), 2.83 (3H, t, J=6 Hz), 3.19–3.48 (2H, m), 3.33 (3H, s), 3.70 (2H, t, J=6 Hz), 4.00–4.28 (3H, m), 4.41 (2H, s), 6.66–7.04 (3H, m), 7.04–7.46 (1H, m), 7.27 (2H, s).

EXAMPLE 36

(a) 1-(3-Allylphenoxy)-3-[1,1-dimethyl-2-(3-chloro-6-pyridazinyloxy)ethylamino]-2-propanol.

NMR(CDCl$_3$) δ: 1.21 (6H, s), 2.69 (2H, broad s), 2.64–2.88 (2H, m), 3.34 (2H, d, J=6 Hz), 3.96 (3H, broad s), 4.32 (2H, s), 4.72–5.26 (2H, m), 5.50–6.30 (1H, m), 6.55–7.40 (4H, m), 6.91 (1H, d, J=9 Hz), 7.32 (1H, d, J=9 Hz).

(b) 1-(3-Allylphenoxy)-3-[1,1-dimethyl-2-(3-hydrazino-6-pyridazinyloxy)ethylamino)-2-propanol hydrochloride.

Melting Point: 181.5°–184.1° C.

NMR(D$_2$O) δ: 1.56 (6H, s), 3.20–3.50 (4H, m), 4.03–4.50 (3H, m), 4.42 (2H, s), 4.90–5.32 (2H, m), 5.50–6.30 (1H, m), 6.60–7.45 (4H, m), 7.27 (2H, s).

EXAMPLE 37

(a) 1-(3-Cyanophenoxy)-3-[1,1-dimethyl-2-(3-isopropylidenehydrazino-6-pyridazinyloxy)ethylamino]-2-propanol.

NMR(CDCl$_3$) δ: 1.21 (6H, s), 1.92 (3H, s), 2.02 (3H, s), 2.50–3.35 (2H, m), 2.65–2.94 (2H, m), 3.98 (3H, broad s), 4.23 (2H, s), 6.88 (1H, d, J=9 Hz), 7.10–7.32 (4H, m), 7.51 (1H, d, J=9 Hz).

(b) 1-(3-Cyanophenoxy)-3-[1,1-dimethyl-2-(3-hydrazino-6-pyridazinyloxy)ethylamino]-2-propanol hydrochloride.

Melting point: 173.7°–176.5° C.

NMR(D$_2$O) δ: 1.58 (6H, s), 3.80–4.05 (2H, m), 4.10–4.60 (3H, m), 4.46 (2H, s), 7.23–7.57 (4H, m), 7.37 (2H, s).

EXAMPLE 38

(a) 1-(3-Ethoxyphenoxy)-3-[1,1-dimethyl-2-(3-chloro-6-pyridazinyloxy)ethylamino]-2-propanol.

NMR(CDCl$_3$) δ: 1.19 (6H, s), 1.37 (3H, t, J=7 Hz), 2.56 (2H, broad s), 2.64–2.92 (2H, m), 3.93 (3H, broad s), 3.97 (2H, q, J=7 Hz), 4.30 (2H, s), 6.32–6.59 (3H, m), 6.90 (1H, d, J=9 Hz), 6.98–7.22 (1H, m), 7.31 (1H, d, J=9 Hz).

(b) 1-(3-Ethoxyphenoxy)-3-[1,1-dimethyl-2-(3-hydrazino-6-pyridazinyloxy)ethylamino]-2-propanol hydrochloride.

NMR(CD$_3$OD) δ: 1.34 (3H, t, J=7 Hz), 1.56 (6H, s), 3.20–3.52 (2H, m), 3.97 (2H, q, J=7 Hz), 3.92–4.32 (3H, m), 4.43 (2H, s), 6.39–6.69 (3H, m), 6.95–7.32 (1H, m), 7.44 (2H, s).

EXAMPLE 39

(a) 1-(2-Cyano-3-methylphenoxy)-3-[1,1-dimethyl-2-(3-chloro-6-pyridazinyloxy)ethylamino]-2-propanol.

NMR(CDCl$_3$) δ: 1.22 (6H, s), 2.49 (3H, s), 2.60–3.10 (4H, m), 4.05 (3H, broad s), 4.32 (2H, s), 6.60–7.51 (3H, m), 6.98 (1H, d, J=9.5 Hz), 7.33 (1H, d, J=9.5 Hz).

(b) 1-(2-Cyano-3-methylphenoxy)-3-[1,1-dimethyl-2-(3-isopropylidenehydrazino-6-pyridazinyloxy)ethylamino]-2-propanol.

NMR(CDCl$_3$) δ: 1.21 (6H, s), 1.92 (3H, s), 2.02 (3H, s), 2.49 (3H, s), 2.55–3.20 (4H, m), 4.05 (3H, broad s), 4.22 (2H, s), 6.65–7.50 (3H, m), 6.90 (1H, d, J=9.5 Hz), 7.47 (1H, d, J=9.5 Hz).

(c) 1-(2-Cyano-3-methylphenoxy)-3-[1,1-dimethyl-2-(3-hydrazino-6-pyridazinyloxy)ethylamino]-2-propanol hydrochloride.

NMR(D$_2$O) δ: 1.57 (6H, s), 2.41 (3H, s), 3.32–3.53 (2H, m), 4.18–4.50 (3H, m), 4.42 (2H, s), 6.80–7.50 (3H, m), 7.22 (2H, s).

EXAMPLE 40

(a) 1-(3-Chloro-2-methylphenoxy)-3-[1,1-dimethyl-2-(3-chloro-6-pyridazinyloxy)ethylamino]-2-propanol.

NMR(CDCl$_3$) δ: 1.20 (6H, s), 2.22 (3H, s), 2.60 (2H, broad s), 2.72–2.96 (2H, m), 3.95 (3H, broad s), 4.31 (2H, s), 6.58–7.10 (3H, m), 6.88 (1H, d, J=9 Hz), 7.31 (1H, d, J=9 Hz).

(b) 1-(3-Chloro-2-methylphenoxy)-3-[1,1-dimethyl-2-(3-isopropylidenehydrazino-6-pyridazinyloxy)ethylamino]-2-propanol.

Melting point: 117.5°–120.0° C.

NMR(CDCl$_3$) δ: 1.21 (6H, s), 1.92 (3H, s), 2.03 (3H, s), 2.24 (3H, s), 2.70–3.12 (2H, m), 2.75–2.98 (2H, m). 3.97 (3H, broad s), 4.23 (2H, s), 6.60–7.29 (3H, m), 6.88 (1H, d, J=9 Hz), 7.49 (1H, d, J=9 Hz).

(c) 1-(3-Chloro-2-methylphenoxy)-3-[1,1-dimethyl-2-(3-hydrazino-6-pyridazinyloxy)ethylamino]-2-propanol hydrochloride.

Melting point: 178.0°–181.0° C.

NMR(D$_2$O) δ: 1.57 (6H, s), 2.10 (3H, s), 3.33–3.57 (2H, m), 4.06–4.36 (3H, m), 4.38 (2H, s), 6.75–7.25 (3H, m). 7.07 (2H, s).

EXAMPLE 41

1-(2,3-Dichlorophenoxy)-3-[1,1-dimethyl-2-(3-hydrazino-6-pyridazinyloxy)ethylamino]-2-propanol hydrochloride.

NMR(CD$_3$OD) δ: 1.57 (6H, s), 3.25–3.50 (2H, m), 4.00–4.41 (3H, m), 4.42 (2H, s), 6.92–7.38 (3H, m), 7.42 (2H, s).

EXAMPLE 42

(a) 1-(2,3-Dimethylphenoxy)-3-[1,1-dimethyl-2-(3-chloro-6-pyridazinyloxy)ethylamino]-2-propanol.

NMR(CDCl$_3$) δ: 1.20 (6H, s), 2.08 (3H, s), 2.23 (3H, s), 2.57 (2H, broad s), 2.72–3.05 (2H, m), 3.95 (3H, broad s), 4.32 (2H, s), 6.54–7.18 (3H, m), 6.88 (1H, d, J=9 Hz), 7.30 (1H, d, J=9 Hz).

(b) 1-(2,3-Dimethylphenoxy)-3-[1,1-dimethyl-2-(3-isopropylidenehydrazino-6-pyridazinyloxy)ethylamino]-2-propanol.

NMR(CD$_3$OD) δ: 1.23 (6H, s), 1.95 (3H, s), 2.02 (3H, s), 2.08 (3H, s), 2.20 (3H, s), 2.60–3.06 (2H, m), 3.95 (3H, broad s), 4.18 (2H, s), 6.55–7.15 (3H, m), 6.88 (1H, d, J=9 Hz), 7.41 (1H, d, J=9 Hz).

(c) 1-(2,3-Dimethylphenoxy)-3-[1,1-dimethyl-2-(3-hydrazino-6-pyridazinyloxy)ethylamino]-2-propanol hydrochloride.

Memting point: 189.2°–190.4° C.

NMR(D₂O) δ: 1.55 (6H, s), 2.00 (3H, s), 2.19 (3H, s), 3.27–3.55 (2H, m), 3.98–4.27 (3H, m), 4.38 (2H, s), 6.60–7.22 (3H, m), 7.04 (2H, s).

EXAMPLE 43

(a) 1-[2-Chloro-4-(2-methoxyethyl)phenoxy]-3-[1,1-dimethyl-2-(3-chloro-6-pyridazinyloxy)ethylamino]-2-propanol.

NMR(CDCl₃) δ: 1.21 (6H, s), 2.54–3.02 (6H, m), 3.32 (3H, s), 3.54 (2H, t, J=6 Hz), 3.98 (3H, broad s), 4.32 (2H, s), 6.65–7.28 (3H, m), 6.90 (1H, d, J=9 Hz), 7.29 (1H, d, J=9 Hz).

(b) 1-[2-Chloro-4-(2-methoxyethyl)phenoxy]-3-[1,1-dimethyl-2-(3-hydrazino-6-pyridazinyloxy)ethylamino]-2-propanol hydrochloride.

NMR(D₂O) δ: 1.57 (6H, s), 2.83 (2H, t, J=6 Hz), 3.36 (3H, s), 3.47 (2H, d, J=4.5 Hz), 3.71 (2H, d, J=6 Hz), 4.15–4.34 (3H, m), 4.47 (2H, s), 6.80–7.40 (3H, m), 7.28 (2H, s).

EXAMPLE 44

(a) 1-(2-Chloro-4-methoxyphenoxy)-3-[1,1-dimethyl-2-(3-chloro-6-pyridazinyloxy)ethylamino]-2-propanol.

NMR(CDCl₃) δ: 1.21 (6H, s), 2.70 (2H, s), 2.70–3.05 (2H, m), 3.73 (3H, s), 3.97 (3H, broad s), 4.32 (2H, s), 6.55–7.00 (4H, m), 7.31 (1H, d, J=9 Hz).

(b) 1-(2-Chloro-4-methoxyphenoxy)-3-[1,1-dimethyl-2-(3-isopropylidenehydrazino-6-pyridazinyloxy)ethylamino]-2-propanol.

NMR(CDCl₃) δ: 1.21 (6H, s), 1.92 (3H, s), 2.01 (3H, s), 2.70–3.10 (2H, m), 3.73 (3H, s), 3.99 (3H, broad s), 4.23 (2H, s), 6.55–6.96 (4H, m), 7.50 (1H, d, J=9 Hz).

(c) 1-(2-Chloro-4-methoxyphenoxy)-3-[1,1-dimethyl-2-(3-hydrazino-6-pyridazinyloxy)ethylamino]-2-propanol hydrochloride.

Melting point: 174.6°–175.6° C.

NMR(D₂O) δ: 1.58 (6H, s), 3.30–3.55 (2H, m), 3.80 (3H, s), 4.00–4.50 (3H, m), 4.44 (2H, s), 6.88–7.05 (3H, m), 7.23 (2H, s).

EXAMPLE 45

(a) 1-(2-Cyano-5-methylphenoxy)-3-[1,1-dimethyl-2-(3-chloro-6-pyridazinyloxy)ethylamino]-2-propanol.

NMR(CDCl₃) δ: 1.23 (6H, s), 2.38 (3H, s), 2.68–3.03 (2H, m), 3.23 (2H, broad s), 4.05 (3H, broad s), 4.33 (2H, s), 6.65–6.91 (2H, m), 7.01 (1H, d, J=9.5 Hz), 7.32 (1H, d, J=9.5 Hz), 7.38 (1H, d, J=8 Hz).

(b) 1-(2-Cyano-5-methylphenoxy)-3-[1,1-dimethyl-2-(3-isopropylidenechydrazino-6-pyridazinyloxy)ethylamino]-2-propanol.

NMR(CDCl₃) δ: 1.27 (6H, s), 1.92 (3H, s), 2.01 (3H, s), 2.37 (3H, s), 2.80–3.12 (2H, m), 3.30–4.50 (2H, m), 4.09 (3H, broad s), 4.30 (2H, s), 6.67–6.90 (2H, m), 6.92 (1H, d, J=9.5 Hz), 7.37 (1H, d, J=8 Hz), 7.49 (1H, d, J=9.5 Hz).

(c) 1-(2-Cyano-5-methylphenoxy)-3-[1,1-dimethyl-2-(3-hydrazino-6-pyrazinyloxy)ethylamino]-2-propanol hydrochloride.

NMR(D₂O) δ: 1.59 (6H, s), 2.40 (3H, s), 3.31–3.56 (2H, m) 4.15–4.56 (3H, m), 4.47 (2H, s), 6.81–7.09 (2H, m), 7.32 (2H, s), 7.46 (1H, d, J=8 Hz).

EXAMPLE 46

(a) 1-(2-Cyano-5-chlorophenoxy)-3-[1,1-dimethyl-2-(3-chloro-6-pyridazinyloxy)ethylamino]-2-propanol.

NMR(CDCl₃) δ: 1.21 (6H, s), 2.52–3.15 (4H, m), 4.08 (3H, broad s), 4.32 (2H, s), 6.79–7.15 (2H, m), 6.98 (1H, d, J=9.5 Hz), 7.36 (1H, d, J=9.5 Hz), 7.45 (1H, d, J=8 Hz).

(b) 1-(2-Cyano-5-chlorophenoxy)-3-[1,1-dimethyl-2-(3-isopropylidenehydrazino-6-pyridazinyloxy)ethylamino]-2-propanol.

NMR(CDCl₃) δ: 1.21 (6H, s), 1.91 (3H, s), 2.02 (3H, s), 2.67–3.35 (4H, m), 4.07 (3H, broad s), 4.23 (2H, s), 6.78–7.12 (2H, m), 6.90 (1H, d, J=9.5 Hz), 7.44 (1H, d, J=8 Hz), 7.49 (1H, d, J=9.5 Hz).

(c) 1-(2-Cyano-5-chlorophenoxy)-3-[1,1-dimethyl-2-(3-hydrazino-6-pyridazinyloxy)ethylamino]-2-propanol hydrochloride.

NMR(D₂O) δ: 1.58 (6H, s), 3.28–3.55 (2H, m), 4.12–4.60 (3H, m), 4.46 (2H, s), 7.14 (1H, d, J=8 Hz), 7.21 (1H, s), 7.39 (2H, s), 7.60 (1H, d, J=8 Hz).

EXAMPLE 47

(a) 1-(2-Chloro-5-methoxyphenoxy)-3-[1,1-dimethyl-2-(3-chloro-6-pyridazinyloxy)ethylamino]-2-propanol.

NMR(CDCl₃) δ: 1.23 (6H, s), 2.88 (4H, broad s), 3.76 (3H, s), 4.00 (3H, broad s), 4.33 (2H, s), 6.40 (1H, q, J=8 Hz, J=3 Hz), 6.46 (1H, d, J=3 Hz), 6.93 (1H, d, J=9 Hz), 7.13 (1H, d, J=8 Hz), 7.31 (1H, d, J=9 Hz).

(b) 1-(2-Chloro-5-methoxyphenoxy)-3-[1,1-dimethyl-2-(3-hydrazino-6-pyridazinyloxy)ethylamino]-2-propanol hydrochloride.

NMR(D₂O) δ: 1.59 (6H, s), 3.30–3.57 (2H, m), 3.85 (3H, s), 4.13–4.39 (3H, m), 4.46 (2H, s), 6.45–6.79 (2H, m), 7.26 (2H, s), 7.30 (1H, d, J=9 Hz).

EXAMPLE 48

(a) 1-(2,5-Dimethylphenoxy)-3-[1,1-dimethyl-2-(3-chloro-6-pyridazinyloxy)ethylamino]-2-propanol.

NMR(CDCl₃) δ: 1.21 (6H, s), 2.13 (3H, s), 2.29 (3H, s), 2.50 (2H, broad s), 2.70–2.90 (2H, m), 3.95 (3H, broad s), 4.32 (2H, s), 6.54–7.10 (3H, m), 6.86 (1H, d, J=9.5 Hz), 7.30 (1H, d, J=9.5 Hz).

(b) 1-(2,5-Dimethylphenoxy)-3-[1,1-dimethyl-2-(3-isopropylidenehydrazino-6-pyridazinyloxy)ethylamino]-2-propanol.

NMR(CDCl₃) δ: 1.20 (6H, s), 1.91 (3H, s), 2.01 (3H, s), 2.13 (3H, s), 2.29 (3H, s), 2.70–2.92 (2H, m), 3.50–4.45 (2H, m), 3.96 (3H, broad s), 4.22 (2H, s), 6.52–7.10 (3H, m), 6.83 (1H, d, J=9.5 Hz), 7.47 (1H, d, J=9.5 Hz).

(c) 1-(2,5-Dimethylphenoxy)-3-[1,1-dimethyl-2-(3-hydrazino-6-pyridazinyloxy)ethylamino]-2-propanol hydrochloride.

Melting point: 194.2°–195.6° C.

NMR(D₂O) δ: 1.58 (6H, s), 2.09 (3H, s), 2.30 (3H, s), 3.30–3.52 (2H, m), 3.95–4.55 (3H, m), 4.40 (2H, s), 6.60–7.10 (3H, m), 7.13 (2H, s).

EXAMPLE 49

1-(2,5-Dichlorophenoxy)-3-[1,1-dimethyl-2-(3-hydrazino-6-pyridazinyloxy)ethylamino]-2-propanol hydrochloride.

NMR(CD₃OD) δ: 1.54 (6H, s), 3.23–3.50 (2H, m), 3.98–4.38 (3H, m), 4.42 (2H, s), 6.94 (1H, q, J=8 Hz, 2 Hz), 7.12 (1H, d, J=2 Hz), 7.32 (1H, d, J=8 Hz), 7.44 (2H, s).

EXAMPLE 50

(a) 1-(2-Chloro-6-methylphenoxy)-3-[1,1-dimethyl-2-(3-chloro-6-pyridazinyloxy)ethylamino]-2-propanol.

NMR(CDCl₃) δ: 1.23 (6H, s), 2.30 (3H, s), 2.70 (2H, broad s), 2.73–2.94 (2H, m), 3.93 (3H, broad s), 4.33 (2H, s), 6.80–7.35 (3H, m), 6.95 (1H, d, J=9 Hz), 7.33 (1H, d, J=9 Hz).

(b) 1-(2-Chloro-6-methylphenoxy)-3-[1,1-dimethyl-2-(3-hydrazino-6-pyridazinyloxy)ethylamino]-2-propanol hydrochloride.

Melting point: 187.3°–188.9° C.

NMR(D₂O) δ: 1.60 (6H, s), 2.31 (3H, s), 3.35–3.60 (2H, m), 4.00–4.50 (3H, m), 4.52 (2H, s), 6.90–7.50 (3H, m), 7.38 (2H, s).

EXAMPLE 51

(a) 1-(2,6-Dichlorophenoxy)-3-[1,1-dimethyl-2-(3-chloro-6-pyridazinyloxy)ethylamino]-2-propanol.

NMR(CDCl₃) δ: 1.25 (6H, s), 2.80–3.00 (2H, m), 3.28 (2H, s), 4.06 (3H, broad s), 4.36 (2H, s), 6.79–7.50 (3H, m), 7.00 (1H, d, J=9 Hz), 7.36 (1H, d, J=6 Hz).

(b) 1-(2,6-Dichlorophenoxy)-3-[1,1-dimethyl-2-(3-hydrazino-6-pyridazinyloxy)ethylamino]-2-propanol hydrochloride.

Melting point: 192.2°–193.2° C.

NMR(D₂O) δ: 1.60 (6H, s), 3.35–3.63 (2H, m), 4.05–4.50 (3H, m), 4.50 (2H, s), 6.95–7.60 (3H, m), 7.40 (2H, s).

EXAMPLE 52

(a) 1-(4-Chloro-3-methoxyphenoxy)-3-[1,1-dimethyl-2-(3-chloro-6-pyridazinyloxy)ethylamino]-2-propanol.

NMR(CDCl₃) δ: 1.22 (6H, s), 2.50–3.05 (4H, m) 3.83 (3H, s), 3.94 (3H, broad s), 4.33 (2H, s), 6.37 (1H, q, J=3 Hz, 8 Hz), 6.49 (1H, d, J=3 Hz), 6.92 (1H, d, J=9 Hz), 7.18 (1H, d, J=8 Hz), 7.34 (1H, d, J=9 Hz).

(b) 1-(4-Chloro-3-methoxyphenoxy)-3-[1,1-dimethyl-2-(3-hydrazino-6-pyridazinyloxy)ethylamino]-2-propanol hydrochloride.

NMR(D₂O) δ: 1.56 (6H, s), 3.30–3.55 (2H, m), 3.84 (3H, s), 4.05–4.35 (3H, m), 6.40–6.62 (2H, m), 7.23 (2H, s), 7.25 (1H, d, J=9 Hz).

EXAMPLE 53

1-(3,5-Dichlorophenoxy)-3-[1,1-dimethyl-2-(3-hydrazino-6-pyridazinyloxy)ethylamino]-2-propanol hydrochloride.

NMR(CD₃OD) δ: 1.56 (6H, s), 3.20–3.50 (2H, m), 3.96–4.30 (3H, m), 4.43 (2H, s), 6.95 (3H, s), 7.48 (2H, s).

EXAMPLE 54

(a) 1-(3,5-Dimethylphenoxy)-3-[1,1-dimethyl-2-(3-chloro-6-pyridazinyloxy)ethylamino]-2-propanol.

NMR(CDCl₃) δ: 1.21 (6H, s), 2.28 (6H, s), 2.48 (2H, broad s), 2.64–2.88 (2H, m), 3.93 (3H, broad s), 4.32 (2H, s), 6.45–6.70 (3H, m), 6.92 (1H, d, J=9 Hz), 7.31 (1H, d, J=9 Hz).

(b) 1-(3,5-Dimethylphenoxy)-3-[1,1-dimethyl-2-(3-hydrazino-6-pyridazinyloxy)ethylamino]-2-propanol hydrochloride.

Melting point: 181.4°–183.0° C.

NMR(D₂O) δ: 1.55 (6H, s), 2.25 (6H, s), 3.25–3.50 (2H, m), 3.98–4.35 (3H, m), 4.39 (2H, s), 6.56 (2H, broad s), 6.68 (1H, broad s), 7.20 (2H, s).

EXAMPLE 55

(a) To a suspension of 1.5 g of 61% sodium hydride in 40 ml of benzene was added dropwise 2.5 g of 2-amino-1-propanol at room temperature. Then, a solution of 5 g of 3,6-dichloropyridazine in 15 ml of benzene was added, and the mixture was refluxed for 1 hour. After cooling, the reaction mixture was washed with water, and dried over magnesium sulfate. After evaporating the solvent, the residue was treated with hydrogen chloride-ether solution to give 2.31 g of 3-(2-aminopropoxy)-6-chloropyridazine hydrochloride.

NMR(D₂O) δ: 1.50 (3H, d, J=7 Hz), 3.36–4.24 (1H, m), 4.56 (2H, d, J=6 Hz), 7.37 (1H, d, J=9 Hz), 7.68 (1H, d, J=9 Hz).

(b) By treating a solution of 1.3 g of 3-(2-aminopropoxy)-6-chloropyridazine obtained in (a) above and 1 g of 1-(2-cyanophenoxy)-2,3-epoxypropane in 20 ml of methanol in the same way as in Example 1, (b) to give 1.01 g of 1-(2-cyanophenoxy)-3-[1-methyl-2-(3-chloro-6-pyridazinyloxy)ethylamino]-2-propanol.

NMR(CDCl₃) δ: 1.20 (3H, d, J=6.5 Hz), 2.76 (2H, broad s), 2.87–3.46 (3H, m), 4.09 (3H, broad s), 4.41 (2H, d, J=5 Hz), 6.83–7.70 (4H, m), 6.99 (1H, d, J=9 Hz), 7.37 (1H, d, J=9 Hz).

(c) A mixture of 1.05 g of 1-(2-cyanophenoxy)-3-[1-methyl-2-(3-chloro-6-pyridazinyloxy)ethylamino]-2-propanol obtained in (b) above, 20 ml of hydrazine hydrate and 10 ml of ethanol was treated in the same way as in Example 1, (c) to give 320 mg of 1-(2-cyanophenoxy)-3-[1-methyl-2-(3-isopropylidenehydrazino-6-pyridazinyloxy)ethylamino]-2-propanol having a melting point of 121° to 123° C.

NMR(CDCl₃) δ: 1.17 (3H, d, J=6 Hz), 1.90 (3H, s), 2.01 (3H, s), 2.60–3.90 (2H, m), 2.81–3.40 (3H, m), 4.08 (3H, broad s), 4.29 (2H, d, J=6 Hz), 6.70–7.70 (4H, m), 6.90 (1H, d, J=9 Hz), 7.50 (1H, d, J=9 Hz).

The compounds shown in Examples 56 and 57 were obtained as follows:

In the same way as in Example 2, 3-(2-aminopropoxy)-6-chloropyridazine was reacted with the corresponding epoxide and then the product was coverted into the corresponding hydrazine or hydrazone compound.

EXAMPLE 56

(a) 1-(2-Methylphenoxy)-3-[1-methyl-2-(3-chloro-6-pyridazinyloxy)ethylamino]-2-propanol.

NMR(CDCl₃) δ: 1.18 (3H, d, J=6.5 Hz), 2.20 (3H, s), 2.58 (2H, broad s), 2.80–3.47 (3H, m), 3.99 (3H, broad s), 4.40 (2H, d, J=6 Hz), 6.65–7.35 (4H, m), 6.90 (1H, d, J=9 Hz), 7.31 (1H, d, J=9 Hz).

(b) 1-(2-Methylphenoxy)-3-[1-methyl-2-(3-isopropylidenehydrazino-6-pyridazinyloxy)ethylamino]-2-propanol.

NMR(CDCl$_3$) δ: 1.16 (3H, d, J=6.5 Hz), 1.90 (3H, s), 2.01 (3H, s), 2.21 (3H, s), 2.40–3.50 (2H, m), 2.53–3.46 (3H, m), 3.99 (3H, broad s), 4.30 (2H, d, J=6 Hz), 6.65–7.36 (4H, m), 6.85 (1H, d, J=9 Hz), 7.49 (1H, d, J=9 Hz).

EXAMPLE 57

(a) 1-(2-Chloro-3-methylphenoxy)-3-[1-methyl-2-(3-chloro-6-pyridazinyloxy)ethylamino]-2-propanol.

NMR(CDCl$_3$) δ: 1.21 (3H, d, J=7 Hz), 2.38 (3H, s), 2.83 (2H, s), 2.89–3.48 (3H, m), 4.04 (3H, broad s), 4.42 (2H, d, J=6 Hz), 6.60–7.15 (3H, m), 6.93 (1H, d, J=9 Hz), 7.32 (1H, d, J=9 Hz).

(b) 1-(2-Chloro-3-methylphenoxy)-3-[1-methyl-2-isopropylidenehydrazino-6-pyridazinyloxy)ethylamino]-2-propanol.

Melting point: 131.5°–133.5° C.

NMR (CDCl$_3$) δ: 1.14, 1.19 (3H, double d, J=7 Hz), 1.92 (3H, s), 2.02 (3H, s), 2.38 (3H, s), 2.62–3.50 (2H, m), 2.88–3.78 (3H, m), 4.05 (3H, broad s), 4.34 (2H, d, J=6 Hz), 6.62–7.23 (3H, m), 6.88 (1H, d, J=9 Hz), 7.50 (1H, d, J=9 Hz).

(c) 1-(2-Chloro-3-methylphenoxy)-3-[1-methyl-2-(3-hydrazino-6-pyridazinyloxy)ethylamino]-2-propanol hydrochloride.

Melting point: 168.0°–171.5° C.

NMR(D$_2$O) δ: 1.55, 1.58 (3H, double d, J=7 Hz), 2.35 (3H, s), 3.48–3.70 (3H, m), 4.15–4.39 (3H, m), 4.40–4.70 (2H, m), 6.74–7.50 (5H, m).

EXAMPLE 58

(a) To a suspension of 4.2 g of 61% sodium hydride in 100 ml of benzene was added dropwise 6.2 g of 2-aminoethanol at room temperature. Then, 15 g of 3,6-dichloropyridazine was added, and the mixture was refluxed for 1 hour. After cooling, the reaction mixture was washed with water, and dried over magnesium sulfate. After evaporating the solvent, the residue was treated with hydrogen chrolide-ether solution to give 5.73 g of 3-(2-aminoethoxy)-6-chloropyridazine hydrochloride as crystals.

NMR(D$_2$O) δ: 3.56 (2H, t, J=5 Hz), 4.71 (2H, t, J=5 Hz), 7.35 (1H, d, J=9 Hz), 7.77 (1H, d, J=9 Hz).

(b) A solution of 1.75 g of 3-(2-aminoethoxy)-6-chloropyridazine obtained in (a) above and 800 mg of 1-(2-cyanophenoxy)-2,3-epoxypropane in 10 ml of ethanol was treated in the same way as in Example 1, (b) to give 862 mg of 1-(2-cyanophenoxy)-3-[2-(3-chloro-6-pyridazinyloxy)ethylamino]-2-propanol.

NMR(CDCl$_3$) δ: 2.90 (2H, broad s), 2.96 (2H, d, J=5 Hz), 3.10 (2H, t, J=6 Hz), 4.11 (3H, broad s), 4.59 (2H, t, J=6 Hz), 6.81–7.70 (4H, m), 6.97 (1H, d, J=9 Hz), 7.35 (1H, d, J=9 Hz).

(c) A mixture of 1.2 g of 1-(2-cyanophenoxy)-3-[2-(3-chloro-6-pyridazinyloxy)ethylamino]-2-propanol obtained in (b) above, 6 ml of hydrazine hydrate and 12 ml of ethanol was treated in the same way as in Example 1, (c) to give 201 mg of 1-(2-cyanophenoxy)-3-[2-(3-isopropylidenehydrazino-6-pyridazinyloxy)ethylamino]-2-propanol.

NMR(CDCl$_3$) δ: 1.59 (3H, s), 2.05 (3H, s), 2.85–3.40 (2H, m), 3.03 (2H, d, J=5 Hz), 3.12 (2H, t, J=6 Hz), 4.15 (3H, broad s), 4.52 (2H, t, J=6 Hz), 6.78–7.70 (4H, m), 6.88 (1H, d, J=9 Hz), 7.50 (1H, d, J=9 Hz).

EXAMPLE 59

In the same way as in Example 58, the following compounds were obtained.

(a) 1-(2-Methylphenoxy)-3-[2-(3-chloro-6-pyridazinyloxy)ethylamino]-2-propanol.

NMR(CDCl$_3$) δ: 2.23 (3H, s), 2.60 (2H, broad s), 2.94 (2H, d, J=5 Hz), 3.09 (2H, t, J=6 Hz), 4.01 (3H, broad s), 4.60 (2H, t, J=6 Hz), 6.66–7.32 (4H, m), 6.91 (1H, d, J=9 Hz), 7.32 (1H, d, J=9 Hz).

(b) 1-(2-Methylphenoxy)-3-[2-(3-isopropylidenehydrazino-6-pyridazinyloxy)ethylamino]-2-propanol.

NMR(CDCl$_3$) δ: 1.92 (3H, s), 2.03 (3H, s), 2.22 (3H, s), 2.58–3.35 (2H, m), 2.93 (2H, d, J=5 Hz), 3.07 (2H, t, J=6 Hz), 4.01 (3H, broad s), 4.50 (2H, t, J=6 Hz), 6.60–7.30 (4H, m), 6.87 (1H, d, J=9 Hz), 7.50 (1H, d, J=9 Hz).

EXAMPLE 60

(a) To a suspension of 1.32 g of 61% sodium hydride in 20 ml of benzene was added dropwise at room tmperature a solution of 2.6 g of 2-methyl-2-aminopropanethiol in 10 ml of benzene. Then, a solution of 4.1 g of 3,6-dichloropyridazine in 10 ml of benzene was added, and the mixture was refluxed for 6 hours. After cooling, the reaction mixture was washed with water and dried over magnesium sulfate. The solvent was evaporated to give 1.96 g of 3-(2-amino-2-methylpropylthio)-6-chloropyridazine.

NMR(CDCl$_3$) δ: 1.24 (6H, s), 1.42 (2H, s), 3.51 (2H, s), 7.15 (1H, d, J=9 Hz), 7.35 (1H, d, J=9 Hz).

(b) A solution of 980 mg of 3-(2-amino-2-methylpropylthio)-6-chloropyridazine and 960 mg of 1-[2-(2-methoxyethyl)phenoxy]-2,3-epoxypropane in 60 ml of methanol was treated in the same way as in Example 1, (b) to give 534 mg of 1-[2-(2-methoxyethyl)phenoxy]-3-[1,1-dimethyl-2-(3-chloro-6-pyridazinylthio)ethylamino]-2-propanol.

NMR(CDCl$_3$) δ: 1.25 (6H, s), 2.34–2.75 (2H, m), 2.70–3.10 (4H, m), 3.32 (3H, s), 3.58 (2H, s), 3.58 (2H, t, J=6 Hz), 3.98 (3H, broad s), 6.69–7.40 (4H, m), 7.21 (2H, s).

(c) A mixture of 525 mg of 1-[2-(2-methoxyethyl)phenoxy]-3-[1,1-dimethyl-2-(3-chloro-6-pyridazinylthio)ethylamino]-2-propanol obtained in (b) above, 12 ml of hydrazine hydrate and 12 ml of ethanol was treated in the same way as in Example 1, (c) to give 498 mg of 1-[2-(2-methoxyethyl)phenoxy]-3-[1,1-dimethyl-2-(3-isopropylidenehydrazino-6-pyridazinylthio)ethylamino]-2-propanol.

NMR(CDCl$_3$) δ: 1.21 (6H, s), 1.89 (3H, s), 2.01 (3H, s), 2.10–3.10 (2H, m), 2.56–3.10 (4H, m), 3.30 (3H, s), 3.46 (2H, s), 3.57 (2H, t, J=6 Hz), 3.96 (3H, broad s), 6.65–7.35 (6H, m).

(d) A mixture of 575 mg of 1-[2-(2-methoxyethyl)phenoxy]-3-[1,1-dimethyl-2-(3-isopropylidenehydrazino-6-pyridazinylthio)ethylamino]-2-propanol obtained in (c) above, 12 ml of hydrazine hydrate and 12 ml of ethanol was treated in the same way as in Example 1, (d) to give 550 mg of 1-[2-(2-methoxyethyl)phenoxy]-

3-[1,1-dimethyl-2-(3-hydrazino-6-pyridazinylthio)-ethylamino]-2-propanol hydrochloride.

NMR(D$_2$O) δ: 1.59 and (6H, s), 2.90 (2H, t, J=7 Hz), 3.25–3.90 (4H, m), 3.38 (3H, s), 3.71 (2H, s), 4.02–4.48 (3H, m), 6.82–7.53 (4H, m), 7.25 (1H, d, J=9 Hz), 7.55 (1H, d, J=9 Hz).

In the same way as in Example 60, the compounds shown in Examples 61 to 63 were obtained.

EXAMPLE 61

(a) 1(2-Methylphenoxy)-3-[1,1-dimethyl-2-(3-chloro-6-pyridazinylthio)ethylamino]-2-propanol.

NMR(CDCl$_3$) δ: 1.23 (6H, s), 2.19 (3H, s), 2.56 (2H, broad s), 2.72–2.90 (2H, m), 3.56 (2H, s), 3.97 (3H, broad s), 6.60–7.40 (4H, m), 7.18 (2H, s).

(b) 1-(2-Methylphenoxy)-3-[1,1-dimethyl-2-(3-hydrazino-6-pyridazinylthio)ethylamino]-2-propanol hydrochloride.

Melting point: 207°–210° C.

NMR(D$_2$O) δ: 1.57 (6H, s), 2.20 (3H, s), 3.30–3.54 (2H, m), 3.68 (2H, s), 4.04–4.50 (3H, m), 6.80–7.35 (4H, m), 7.14 (1H, d, J=9 Hz), 7.45 (1H, d, J=9 Hz).

EXAMPLE 62

(a) 1-(2-Chloro-3-methylphenoxy)-3-[1,1-dimethyl-2-(3-chloro-6-pyridazinylthio)ethylamino]-2-propanol.

NMR(CDCl$_3$) δ: 1.25 (6H, s), 2.37 (3H, s), 2.50–2.80 (2H, m), 2.77–2.95 (2H, m), 3.57 (2H, s), 4.00 (3H, broad s), 6.62–7.15 (3H, m), 7.19 (2H, s).

(b) 1-(2-Chloro-3-methylphenoxy)-3-[1,1-dimethyl-2-(3-hydrazino-6-pyridazinylthio)ethylamino]-2-propanol hydrochloride.

NMR(D$_2$O) δ: 1.67 (6H, s), 2.40 (3H, s), 3.43–3.70 (2H, m), 3.75 (2H, s), 4.10–4.65 (3H, m), 6.80–7.48 (3H, m), 7.19 (1H, d, J=9 Hz), 7.45 (1H, d, J=9 Hz).

EXAMPLE 63

(a) 1-(2-Chloro-5-methylphenoxy)-3-[1,1-dimethyl-2-(3-chloro-6-pyridazinylthio)ethylamino]-2-propanol.

NMR(CDCl$_3$) δ: 1.22 (6H, s), 2.30 (3H, s), 2.40–2.79 (2H, m), 2.78–2.95 (2H, m), 3.56 (2H, s), 3.98 (3H, broad s), 6.66 (1H, d, J=8 Hz), 6.72 (1H, s), 7.15 (1H, d, J=8 Hz), 7.18 (2H, s).

(b) 1-(2-Chloro-5-methylphenoxy)-3-[1,1-dimethyl-2-(3-isopropylidenehydrazino-6-pyridazinylthio)ethylamino]-2-propanol.

NMR(CDCl$_3$) δ: 1.22 (6H, s), 1.92 (3H, s), 2.03 (3H, s), 2.30 (3H, s), 2.72–2.90 (2H, m), 2.45–3.15 (2H, m), 3.48 (2H, s), 4.00 (3H, broad s), 6.68 (1H, d, J=8 Hz), 6.73 (1H, s), 7.17 (1H, d, J=8 Hz), 7.25 (2H, s).

(c) 1-(2-Chloro-5-methylphenoxy)-3-[1,1-dimethyl-2-(3-hydrazino-6-pyridazinylthio)ethylamino]-2-propanol hydrochloride.

NMR(D$_2$O) δ: 1.61 (6H, s), 2.36 (3H, s), 3.51 (2H, d, J=5 Hz), 3.72 (2H, s), 4.08–4.57 (3H, m), 6.70–7.60 (3H, m), 7.15 (1H, d, J=9 Hz), 7.41 (1H, d, J=9 Hz).

EXAMPLE 64

(a) A mixture of 0.62 g of 60% sodium hydride, 1.91 g of 3,6-dichloropyridazine and 10 ml of benzene was stirred while being cooled with ice, and a solution consisting of 1.32 g of 3-amino-3-methylbutanol, 3 ml of t-butanol and 5 ml of benzene was added dropwise. After stirring at room temperature for 30 minutes, ether was added to the reaction mixture, and the solid was removed by filtration with Hyflo Super-Cel. The filtrate was concentrated under reduced pressure. n-Hexane was added to the resulting oily product, and the mixture was allowed to stand to give 2.34 g of 3-(3-amino-3-methylbutoxy)-6-chloropyridazine as colorless crystals having a melting point of 63.5° to 65.0° C.

NMR(CDCl$_3$) δ: 1.20 (6H, s), 1.32 (2H, broad s), 1.90 (2H, t, J=7 Hz), 4.61 (2H, t, J=7 Hz), 6.88 (1H, d, J=9 Hz) 7.33 (1H, d, J=9 Hz).

(b) A mixture of 645 mg of 3-(3-amino-3-methylbutoxy)-6-chloropyridazine, 650 mg of 1-(2-methylphenoxy)-2,3-epoxypropane and 15 ml of methanol was refluxed for 5 hours, and the solvent was evaporated under reduced pressure. A solution of the residue in benzene was extracted with 1N hydrochloric acid. The aqueous layer was extracted with chloroform, and the organic layer was washed with 5% sodium carbonate, and dried over anhydrous sodium sulfate. The solvent was evaporated to give 938 mg of 1-(2-methylphenoxy)-3-[1,1-dimethyl-3-(chloro-6-pyridazinyloxy)-propylamino]-2-propanol as an oil.

NMR(CDCl$_3$) δ: 1.25 (6H, s), 2.01 (2H, t, J=7 Hz), 2.20 (3H, s), 2.80–3.02 (2H, m), 3.57 (2H, broad s), 4.02 (3H, broad s), 4.60 (2H, t, J=7 Hz), 6.65–7.30 (4H, m), 6.89 (1H, d, J=9 Hz), 7.30 (1H, d, J=9 Hz).

(c) A mixture of 850 mg of 1-(2-methylphenoxy)-3-[1,1-dimethyl-3-(3-chloro-6-pyridazinyloxy)-propylamino]-2-propanol, 15 ml of hydrazine hydrate and 15 ml of ethanol was refluxed for 6 hours. The reaction mixture was concentrated under reduced pressure. A solution of the residue in chloroform was washed with water and dried over anhydrous sodium sulfate. The solvent was evaporated under reduced pressure. Acetone was added to the resulting oily product, and the mixture was left at room temperature for 30 minutes. The solvent was then evaporated under reduced pressure, and the residue was purified by thin-layer chromatography (silica gel (Merck GF$_{254}$); chloroform/methanol=9/1) to give 190 mg of 1-(2-methylphenoxy)-3-[1,1-dimethyl-3-(3-isopropylidenehydrazino-6-pyridazinyloxy)propylamino]-2-propanol as a yellow oil.

NMR(CDCl$_3$) δ: 1.21 (6H, s), 1.91 (3H, s), 1.95 (2H, t, J=7 Hz), 2.02 (3H, s), 2.21 (3H, s), 2.78–3.10 (2H, m), 3.15 (2H, broad s), 4.02 (3H, broad s), 4.50 (2H, t, J=7 Hz), 6.65–7.30 (4H, m), 6.83 (1H, d, J=9 Hz), 7.46 (1H, d, J=9 Hz).

(d) A mixture of 260 mg of 1-(2-methylphenoxy)-3-[1,1-dimethyl-3-(3-isopropylidenehydrazino-6-pyridazinyloxy)propylamino]-2-propanol, 3 ml of hydrazine hydrate and 10 ml of ethanol was refluxed for 2 hours. The solvent was evaporated under reduced pressure. A solution of the residue in chloroform was washed with water and dried over anhydrous magnesium sulfate. The solvent was evaporated under reduced pressure, and the residue was dissolved in 5 ml of ethanol. After addition of 1.9 ml of 2N-hydrochloric acid, the solvent was evaporated under reduced pressure. The product was dissolved in n-propanol/benzene, and allowed to stand at 5° C. There was obtained 192 mg of 1-(2-methylphenoxy)-3-[1,1-dimethyl-3-(3-hydrazino-6-pyridazinyloxy)propylamino]-2-propanol hydrochloride as colorless crystals having a melting point of 182.1° to 184.7° C.

NMR(D$_2$O) δ: 1.53 (6H, s), 2.22 (3H, s), 2.30 (2H, t, J=7 Hz), 3.25–3.55 (2H, m), 4.04–4.60 (3H, m), 4.52 (2H, t, J=7 Hz), 6.76–7.40 (4H, m), 7.32 (2H, m).

In the same way as in Example 64, the compounds shown in Examples 65 to 68 were obtained.

EXAMPLE 65

(a) 1-(2-Chlorophenoxy)-3-[1,1-dimethyl-3-(3-chloro-6-pyridazinyloxy)propylamino]-2-propanol.

NMR(CDCl$_3$) δ: 1.19 (6H, s), 1.93 (2H, t, J=7 Hz), 2.56 (2H, broad s), 2.73–3.03 (2H, m), 4.04 (3H, broad s), 4.59 (2H, t, J=7 Hz), 6.78–7.45 (4H, m), 6.88 (1H, d, J=9 Hz), 7.29 (1H, d, J=9 Hz).

(b) 1-(2-Chlorophenoxy)-3-[1,1-dimethyl-3-(3-isopropylidenehydrazino-6-pyridazinyloxy)propylamino]-2-propanol.

NMR(CDCl$_3$) δ: 1.19 (6H, s), 1.90 (2H, t, J=7 Hz), 1.91 (3H, s), 2.01 (3H, s), 2.43–3.20 (2H, m), 2.78–3.00 (2H, m), 4.04 (3H, broad s), 4.49 (2H, t, J=7 Hz), 6.80–7.50 (4H, m), 6.82 (1H, d, J=9 Hz), 7.46 (1H, d, J=9 Hz).

(c) 1-(2-Chlorophenoxy)-3-[1,1-dimethyl-3-(3-hydrazino-6-pyridazinyloxy)propylamino]-2-propanol hydrochloride.

Melting point: 138.3°–140.2° C.

NMR(D$_2$O) δ: 1.56 (6H, s), 2.30 (2H, t, J=7 Hz), 3.40–3.60 (2H, m), 4.20–4.70 (3H, m), 4.52 (2H, t, J=7 Hz), 6.98–7.50 (4H, m), 7.30 (2H, s).

EXAMPLE 66

(a) 1-(2-Cyanophenoxy)-3-[1,1-dimethyl-3-(3-isopropylidenehydrazino-6-pyridazinyloxy)propylamino]-2-propanol.

Melting point: 101.1°–104.9° C.

NMR(CDCl$_3$) δ: 1.20 (6H, s), 1.90 (3H, s), 1.93 (2H, t, J=7 Hz), 2.01 (3H, s), 2.68–3.00 (2H, m), 3.05 (2H, broad s), 4.10 (3H, broad s), 4.50 (2H, t, J=7 Hz), 6.80–7.70 (4H, m), 6.84 (1H, d, J=9 Hz), 7.47 (1H, d, J=9 Hz).

(b) 1-(2-Cyanophenoxy)-3-[1,1-dimethyl-3-(3-hydrazino-6-pyridazinyloxy)propylamino]-2-propanol hydrochloride.

Melting point: 147.1°–149.7° C.

NMR(D$_2$O) δ: 1.59 (6H, s), 2.34 (2H, t, J=6 Hz), 3.35–3.65 (2H, m), 4.20–4.70 (3H, m), 4.57 (2H, t, J=6 Hz), 7.00–7.90 (4H, m), 7.42 (2H, s).

EXAMPLE 67

(a) 1-(2-Chloro-3-methylphenoxy)-3-[1,1-dimethyl-3-(3-chloro-6-pyridazinyloxy)propylamino]-2-propanol.

NMR(CDCl$_3$) δ: 1.19 (6H, s), 1.94 (2H, t, J=7 Hz), 2.35 (3H, s), 2.52 (2H, broad s), 2.80–2.96 (2H, m), 4.04 (3H, broad s), 4.59 (2H, t, J=7 Hz), 6.65–7.20 (3H, m), 6.87 (1H, d, J=9 Hz), 7.28 (1H, d, J=9 Hz).

(b) 1-(2-Chloro-3-methylphenoxy)-3-[1,1-dimethyl-3-(3-isopropylidenehydrazino-6-pyridazinyloxy)propylamino]-2-propanol.

NMR(CDCl$_3$) δ: 1.20 (6H, s), 1.90 (3H, s), 1.95 (2H, t, J=7 Hz), 2.01 (3H, s), 2.35 (3H, s), 2.75–3.00 (2H, m), 3.00 (2H, broad s), 4.05 (3H, broad s), 4.49 (2H, t, J=7 Hz), 6.60–7.15 (3H, m), 6.82 (1H, d, J=9 Hz), 7.47 (1H, d, J=9 Hz).

(c) 1-(2-Chloro-3-methylphenoxy)-3-[1,1-dimethyl-3-(3-hydrazino-6-pyridazinyloxy)propylamino]-2-propanol hydrochloride.

Melting point: 172.1°–175.2° C.

NMR(D$_2$O) δ: 1.58 (6H, s), 2.30 (3H, s), 2.32 (2H, t, J=6 Hz), 3.43–3.72 (2H, m), 4.20–4.70 (3H, m), 4.52 (2H, t, J=6 Hz), 6.85–7.35 (3H, m), 7.18 (2H, s).

EXAMPLE 68

(a) 1-(2-Chloro-5-methylphenoxy)-3-[1,1-dimethyl-3-(3-chloro-6-pyridazinyloxy)propylamino]-2-propanol.

NMR(CDCl$_3$) δ: 1.18 (6H, s), 1.93 (2H, t, J=7 Hz), 2.30 (3H, s), 2.70 (2H, broad s), 2.65–2.95 (2H, m), 4.02 (3H, broad s). 4.58 (2H, t, J=7 Hz), 6.55–7.30 (3H, m), 6.88 (1H, d, J=9 Hz), 7.29 (1H, d, J=9 Hz).

(b) 1-(2-Chloro-5-methylphenoxy)-3-[1,1-dimethyl-3-(3-isopropylidenehydrazino-6-pyridazinyloxy)propylamino]-2-propanol.

NMR(CDCl$_3$) δ: 1.21 (6H, s), 1.91 (3H, s), 1.95 (2H, t, J=7 Hz), 2.01 (3H, s), 2.82–3.00 (2H, m), 3.30 (2H, broad s), 4.05 (3H, broad s), 4.50 (2H, t, J=7 Hz), 6.55–7.30 (3H, m), 6.84 (1H, d, J=9 Hz), 7.46 (1H, d, J=9 Hz).

(c) 1-(2-Chloro-5-methylphenoxy)-3-[1,1-dimethyl-3-(3-hydrazino-6-pyridazinyloxy)propylamino]-2-propanol hydrochloride.

Melting point: 191.3°–194.4° C.

NMR(D$_2$O) δ: 1.58 (6H, s), 2.32 (2H, t, J=6 Hz), 2.35 (3H, s), 3.37–3.62 (2H, m), 4.18–4.70 (3H, m), 4.52 (2H, t, J=6 Hz), 6.70–7.40 (3H, m), 7.28 (2H, s).

EXAMPLE 69

(a) In the same way as in Example 64, (a), 3-(3-aminobutoxy)-6-chloropyridazine was produced by using 3-aminobutanol and 3,6-dichloropyridazine.

NMR(CDCl$_3$) δ: 1.14 (3H, d, J=6 Hz), 1.50 (2H, s), 1.85 (2H, q, J=6 Hz), 3.09 (1H, quintet, J=6 Hz), 4.58 (2H, t, J=6 Hz), 6.94 (1H, d, J=9 Hz), 7.36 (1H, d, J=9 Hz).

In the same way as in Example 2, the following compound (b) was derived from 3-(3-aminobutoxy)-6-chloropyridazine and 1-(2-cyanophenoxy)-2,3-epoxypropane, and then the compound (b) was converted into the corresponding hydrazone (c).

(b) 1-(2-Cyanophenoxy)-3-[1-methyl-3-(3-chloro-6-pyridazinyloxy)propylamino]-2-propanol.

NMR(CDCl$_3$) δ: 1.16 (3H, d, J=7 Hz), 1.94 (2H, q, J=7 Hz), 2.55–3.20 (3H, m), 2.69 (2H, s), 4.10 (3H, broad s), 4.60 (2H, t, J=7 Hz), 6.83–7.70 (4H, m), 6.92 (1H, d, J=9 Hz), 7.36 (1H, d, J=9 Hz).

(c) 1-(2-Cyanophenoxy)-3-[1-methyl-3-(3-isopropylidenehydrazino-6-pyridazinyloxy)propylamino]-2-propanol.

NMR(CDCl$_3$) δ: 1.16 (3H, d, J=6 Hz), 1.67–2.20 (2H, m), 1.93 (3H, s), 2.03 (3H, s), 2.50–3.80 (5H, m), 4.11 (3H, broad s), 4.49 (2H, t, J=6 Hz), 6.78–7.70 (4H, m), 6.88 (1H, d, J=9 Hz), 7.51 (1H, d, J=9 Hz).

EXAMPLE 70

The following compounds were obtained in the same way as in Example 64.

(a) 1-(2-Chloro-3-methylphenoxy)-3-[1-methyl-3-(3-isopropylidenehydrazino-6-pyridazinyloxy)-propylamino]-2-propanol.

NMR(CDCl$_3$) δ: 1.16 (3H, d, J=7 Hz), 1.65–2.12 (2H, m), 1.90 (3H, s), 2.00 (3H, s), 2.35 (3H, s), 2.70–3.70 (5H, m), 4.03 (3H, broad s), 4.48 (2H, t, J=7 Hz), 6.63–7.17 (3H, m), 6.83 (1H, d, J=9 Hz), 7.47 (1H, d, J=9 Hz).

(b) 1-(2-Chloro-3-methylphenoxy)-3-[1-methyl-3-(3-hydrazino-6-pyridazinyloxy)propylamino]-2-propanol.
Melting point: 152.7°–154.4° C.

NMR(D$_2$O) δ: 1.50 (3H, d, J=7 Hz), 2.12–2.50 (2H, m), 2.31 (3H, s), 3.31–4.07 (3H, m), 4.10–4.63 (3H, m), 4.48 (2H, t, J=6 Hz), 6.82–7.33 (3H, m), 7.20 (2H, s).

EXAMPLE 71

(a) In the same way as in Example 64, (a), 3-(3-aminopropoxy)-6-chloropyridazine was produced from 3-aminopropanol and 3,6-dichloropyridazine.

NMR(CDCl$_3$) δ: 1.37 (2H, s), 1.96 (2H, quintet, J=7 Hz), 2.89 (2H, t, J=7 Hz), 4.56 (2H, t, J=7 Hz), 6.92 (1H, d, J=9 Hz), 7.37 (1H, d, J=9 Hz).

The following compounds were obtained from 3-(3-aminopropoxy)-6-chloropyridazine obtained in (a) above and 1-(2-chloro-5-methylphenoxy)-2,3-epoxypropane in the same way as in Example 64, (b), (c) and (d).

(b) 1-(2-Chloro-5-methylphenoxy)-3-[3-(3-chloro-6-pyridazinyloxy)propylamino]-2-propanol.

NMR(CDCl$_3$) δ: 2.00 (2H, quintet, J=6 Hz), 2.30 (3H, s), 2.43–3.10 (6H, m), 4.03 (3H, broad s), 4.53 (2H, t, J=6 Hz), 6.55–7.40 (3H, m), 6.87 (1H, d, J=9 Hz), 7.32 (1H, d, J=9 Hz).

(c) 1-(2-Chloro-5-methylphenoxy)-3-[3-(3-isopropylidenehydrazino-6-pyridazinyloxy)propylamino]-2-propanol.

NMR(CDCl$_3$) δ: 1.70–2.20 (2H, m), 1.91 (3H, s), 2.02 (3H, s), 2.30 (3H, s), 2.40–3.10 (6H, m), 4.03 (3H, broad s), 4.45 (3H, t, J=6 Hz), 6.55–7.30 (3H, m), 6.85 (1H, d, J=9 Hz), 7.50 (1H, d, J=9 Hz).

(d) 1-(2-Chloro-5-methylphenoxy)-3-[3-(3-hydrazino-6-pyridazinyloxy)propylamino]-2-propanol hydrochloride.

NMR(D$_2$O) δ: 2.05–2.60 (2H, m), 2.35 (3H, s), 3.20–3.65 (4H, m), 4.05–4.65 (3H, m), 4.47 (2H, t, J=6 Hz), 6.75–7.40 (3H, m), 7.32 (2H, s).

EXAMPLE 72

(a) A micture of 4.3 g of 1-(2-methylphenoxy)-2,3-epoxypropane, 7.03 g of N,N-dibenzyl-2-methyl-1,2-propanediamine and 50 ml of ethanol was refluxed for 20 hours, and the solvent was evaporated under reduced pressure. To a benzene solution of the residue was added 1N hydrochloric acid, to deposit an oily material. After removal of the benzene layer, the residue was extracted with chloroform. The organic layer was washed with 5% sodium carbonate and dried over anhydrous sodium sulfate. The solvent was evaporated to give a colorless oily product. The product was chromatographed on a column of silica gel using chloroform as an eluent. 7.3 g of 1-(2-methylphenoxy)-3-(1,1-dimethyl-2-dibenzylaminoethylamino)-2-propanol was obtained from the eluate.

NMR(CDCl$_3$) δ: 1.00 (6H, s), 2.20 (3H, s), 2.40–2.80 (4H, m), 2.54 (2H, s), 3.62 (4H, s), 3.80 (3H, broad s), 6.60–7.42 (4H, m), 7.26 (10H, s).

(b) Concentrated hydrochloric acid (1.4 ml) and 5% palladium carbon was added to a solution of 3 g of 1-(2-methylphenoxy)-3-(1,1-dimethyl-2-dibenzylaminoethylamino)-2-propanol in 10 ml of ethanol, and the mixture was hydrogenated at room temperature for 24 hours. After the catalyst was removed by filtration, the filtrate was concentrated under reduced pressure. The residue was dissolved in water, made alkaline with potassium carbonate, then extracted with chloroform, and dried over anhydrous magnesium sulfate. 1.585 g of 1-(2-methylphenoxy)-3-(1,1-dimethyl-2-aminoethylamino)-2-propanol was obtained as a colorless oil.

NMR(CDCl$_3$) δ: 1.03 (6H, s), 2.08 (4H, broad s), 2.22 (3H, s), 2.56 (2H, s), 2.63–2.83 (2H, m), 3.97 (3H, broad s), 6.65–7.30 (4H, m).

(c) To 1.58 g of 1-(2-methylphenoxy)-3-(1,1-dimethyl-2-aminoethylamino)-2-propanol heated at 110° C. in an oil bath with stirring was added 934 mg of 3,6-dichloropyridazine little by little. After heating at 110° C. for 1 hour, the reaction mixture was dissolved in benzene, and extracted with 1N hydrochloric acid. The aqueous layer was made alkaline with potassium carbonate, and extracted with chloroform. The chloroform layer was dried over anhydrous magnesium sulfate, and the solvent was evaporated to give 1.55 g of 1-(2-methylphenoxy)-3-[1,1-dimethyl-2-(3-chloro-6-pyridazinylamino)ethylamino]-2-propanol as an oil.

NMR(CDCl$_3$) δ: 1.24 (6H, s), 2.13 (3H, s), 2.77–3.03 (2H, m), 3.30–3.58 (2H, d, J=6 Hz), 3.69–4.32 (6H, m), 6.62–7.32 (4H, m), 6.73 (1H, d, J=9 Hz), 7.00 (1H, d, J=9 Hz).

(d) To a solution of 140 mg of 1-(2-methylphenoxy)-3-[1,1-dimethyl-2-(3-chloro-6-pyridazinylamino)ethylamino]-2-propanol in ethanol was added a saturated ether solution of hydrogen chloride. After removal of the solvent, 80 mg of ethyl carbazinate was added to the residue. The mixture was heated at 140° C. for 2 hours, then dissolved in chloroform, washed with 5% sodium carbonate, and dried over anhydrous sodium sulfate. The resulting crude product was purified by thin-layer chromatography [silica gel (Merck GF$_{254}$); chloroform/methanol=4/1] to give 66 mg of 1-(2-methylphenoxy)-3-[1,1,-dimethyl-2-(3-ethoxycarbonylhydrazino-6-pyridazinylamino)-ethylamino]-2-propanol.

(e) A solution of 66 mg of 1-(2-methylphenoxy)-3-[1,1,-dimethyl-2-(3-ethoxycarbonylhydrazino-6-pyridazinylamino)ethylamino]-2-propanol in 5 ml of 10% hydrochloric acid was refluxed for 5 hours. After the solvent was evaporated under reduced pressure, the residue was recrystallized from ethanol to give 31 mg of 1-(2-methylphenoxy)-3-[1,1-dimethyl-2-(3-hydrazino-6-pyridazinylamino)ethylamino]-2-propanol hydrochloride as colorless crystals.

Melting point: 164.4°–166.9° C.

NMR(D$_2$O) δ: 1.53 (6H, s), 2.21 (3H, s), 3.48 (2H, d, J=5 Hz), 3.75 (2H, broad s), 4.13 (2H, d, J=5 Hz), 4.20–4.60 (1H, m), 6.70–7.35 (4H, m), 7.09 (1H, d, J=9 Hz), 7.29 (1H, d, J=9 Hz).

(f) A solusion of 1-(2-methylphenoxy)-3-[1,1-dimethyl-2-(3-hydrazino-6-pyridazinylamino)ethylamino]-2-propanol hydrochloride in water was made alkaline with potassium carbonate, extracted with chloroform and dried over anhydrous sodium sulfate. The resulting free base was treated with acetone to give 1-(2-methylphenoxy)-3-[1,1-dimethyl-2-(3-isopropylidenehydrazino-6-pyridazinylamino)ethylamino]-2-propanol.

NMR(CDCl$_3$) δ: 1.17 (6H, s), 1.87 (3H, s), 1.98 (3H, s), 2.16 (3H, s), 2.70–3.05 (2H, m), 3.33 (2H, broad s), 4.01 (3H, broad s), 6.50–7.30 (4H, m), 6.62 (1H, d, J=9 Hz), 7.32 (1H, d, J=9 Hz).

EXAMPLE 73

In the same was as in Example 72, the following compounds were obtained.

(a) 1-(2-Chlorophenoxy)-3-(1,1-dimethyl-2-dibenzylaminoethylamino)-2-propanol.
NMR(CDCl$_3$) δ: 1.00 (6H, s), 2.36 (2H, broad s), 2.43–2.65 (2H, m), 2.52 (2H, s), 3.63 (4H, s), 3.87 (3H, broad s), 6.68–7.46 (4H, m), 7.28 (10H, s).

(b) 1-(2-Chlorophenoxy)-3-(1,1-dimethyl-2-aminoethylamino)-2-propanol.
NMR(CDCl$_3$) δ: 1.05 (6H, s), 2.17 (4H, broad s), 2.57 (2H, s), 2.60–2.95 (2H, m), 3.97 (3H, broad s), 6.70–7.45 (4H, m).

(c) 1-(2-Chlorophenoxy)-3-[1,1-dimethyl-2-(3-hydrazino-6-pyridazinylamino)ethylamino]-2-propanol hydrochloride.
Melting point: 163.4°–166.9° C.
NMR(D$_2$O) δ: 1.52 (6H, s), 3.44 (2H, d, J=5 Hz), 3.74 (2H, s), 4.14 (2H, d, J=5 Hz), 4.20–4.50 (1H, m), 6.86–7.60 (4H, m), 7.20 (1H, d, J=9 Hz), 7.39 (1H, d, J=9 Hz).

EXAMPLE 74

(a) In the same way as in Example 72, (a), 1-(2-methylphenoxy)-3-[1,1-dimethyl-2-(N-methylbenzylamino)ethylamino]-2-propanol was produced by using N-benzyl-N-methyl-2-methyl-1,2-propanediamine instead of N,N-dibenzyl-2-methyl-1,2-propanediamine.
NMR(CDCl$_3$) δ: 1.08 (6H, s), 2.21 (3H, s), 2.26 (3H, s), 2.43 (2H, s), 2.62–2.88 (2H, m), 2.91 (2H, broad s), 3.60 (2H, s), 3.93 (3H, broad s), 6.65–7.40 (4H, m), 7.23 (5H, s).

The following compounds (b), (c), (d), (e) and (f) were produced in the same way as in Example 72, (b), (c), (d), (e) and (f) respectively by using 1-(2-methylphenoxy)-3-[1,1-dimethyl-2-(N-methylbenzylamino)ethylamino]-2-propanol obtained in (a) above.

(b) 1-(2-Methylphenoxy)-3-(1,1-dimethyl-2-methylaminoethylamino)-2-propanol.
NMR(CDCl$_3$) δ: 1.08 (6H, s), 2.23 (3H, s), 2.44 (3H, s), 2.48 (5H, s), 2.62–2.88 (2H, m), 3.96 (3H, broad s), 6.65–7.30 (4H, m).

(c) 1-(2-Methylphenoxy)-3-[1,1-dimethyl-2-[N-(3-chloro-6-pyridazinyl)methylamino]ethylamino]-2-propanol.

NMR(CDCl$_3$) δ: 1.18 (6H, s), 2.20 (3H, s), 2.67 (2H, broad s), 2.78–3.00 (2H, m), 3.13 (3H, s), 3.68 (2H, s), 3.96 (3H, broad s), 6.60–7.30 (4H, m), 6.80 (1H, d, J=9 Hz), 7.12 (1H, d, J=9 Hz).

(d) 1-(2-Methylphenoxy)-3-[1,1-dimethyl-2-[N-(3-ethoxycarbonylhydrazino-6-pyridazinyl)methylamino]ethylamino]-2-propanol.
NMR(CDCl$_3$) δ: 1.16 (6H, s), 1.22 (3H, t, J=7 Hz), 2.20 (3H, s), 2.50–3.30 (4H, m), 3.10 (3H, s), 3.55 (2H, s), 3.96 (3H, broad s), 4.14 (2H, q, J=7 Hz), 6.60–7.30 (4H, m), 6.85 (2H, s).

(e) 1-(2-Methylphenoxy)-3-[1,1-dimethyl-2-[N-(3-hydrazino-6-pyridazinyl)methylamino]ethylamino]-2-propanol.
NMR(D$_2$O) δ: 1.52 (5H, s), 2.20 (3H, s), 3.29 (3H, s), 3.15–3.58 (2H, m), 3.93 (2H, s), 4.00–4.50 (3H, m), 6.80–7.35 (4H, m), 7.29 (1H, d, J=9 Hz), 7.68 (1H, d, J=9 Hz).

(f) 1-(2-Methylphenoxy)-3-[1,1-dimethyl-2-[N-(3-isopropylidenehydrazino-6-pyridazinyl)methylamino]ethylamino]-2-propanol.
NMR(CDCl$_3$) δ: 1.16 (6H, s), 1.88 (3H, s), 2.00 (3H, s), 2.20 (3H, s), 2.66–3.40 (4H, m), 3.10 (3H, s), 3.57 (2H, s), 3.97 (3H, broad s), 6.60–7.40 (4H, m), 6.75 (1H, d, J=9 Hz), 7.36 (1H, d, J=9 Hz).

EXAMPLE 75

In the same way as in Example 72, the following compounds (a), (b), (c), (d) and (e) were obtained.

(a) 1-(2-Methylphenoxy)-3-[1-methyl-3-(N-methylbenzylamino)-propylamino]-2-propanol.
NMR(CDCl$_3$) δ: 1.05 (3H, d, J=6 Hz), 1.58 (2H, q, J=7 Hz), 2.18 (3H, s), 2.22 (3H, s), 2.46 (2H, t, J=7 Hz), 2.50–2.96 (5H, m), 3.45 (2H, m), 3.97 (3H, broad s), 6.65–7.40 (4H, m), 7.27 (5H, s).

(b) 1-(2-Methylphenoxy)-3-(1-methyl-3-methylaminopropylamino)-2-propanol.
NMR(CDCl$_3$) δ: 1.07 (3H, d, J=7 Hz), 1.55 (2H, q, J=6 Hz), 2.21 (3H, s), 2.41 (6H, s), 2.68 (2H, t, J=7 Hz), 2.10–3.00 (3H, m), 3.98 (3H, broad s), 6.60–7.30 (4H, m).

(c) 1-(2-Methylphenoxy)-3-[1-methyl-3-[N-(3-chloro-6-pyridazinyl)methylamino]propylamino]-2-propanol.
NMR(CDCl$_3$) δ: 1.14 (3H, d, J=6 Hz), 1.22 (2H, q, J=7 Hz), 2.21 (3H, s), 2.40–3.00 (3H, m), 2.70 (2H, broad s), 3.08 (3H, s), 3.50–3.90 (2H, m), 4.02 (3H, broad s), 6.62–7.40 (4H, m), 6.74 (1H, d, J=9.5 Hz), 7.14 (1H, d, J=9.5 Hz).

(d) 1-(2-Methylphenoxy)-3-[1-methyl-3-[N-(3-ethoxycarbonylhydrazino-6-pyridazinyl)methylamino]propylamino]-2-propanol.
NMR(CDCl$_3$) δ: 1.11 (3H, d, J=6 Hz), 1.21 (3H, t, J=7 Hz), 1.66 (2H, q, J=7 Hz), 2.20 (3H, s), 2.50–3.10 (3H, m), 2.99 (3H, s), 3.30–3.82 (2H, m), 4.00 (3H, broad s), 4.14 (2H, q, J=7 Hz), 6.60–7.30 (4H, m), 6.81 (2H, s).

(e) 1-(2-Methylphenoxy)-3-[1-methyl-3-[N-(3-hydrazino-6-pyridazinyl)methylamino]propylamino]-2-propanol hydrochloride.
NMR(D$_2$O) δ: 1.47 (3H, d, J=6 Hz), 1.80–2.40 (2H, m), 2.22 (3H, s), 2.70–3.90 (5H, m), 3.23 (3H, s), 4.00–4.60 (3H, m), 6.70–7.90 (6H, m).

EXAMPLE 76

In the same way as in Example 72, the following compounds (a), (b), (c), (d) and (e) were obtained.

(a) 1-(2-Methylphenoxy)-3-(1-methyl-3-dibenzylaminopropylamino)-2-propanol.

NMR(CDCl$_3$) δ: 0.94 (3H, d, J=6 Hz), 1.33–1.85 (2H, m), 2.21 (3H, s), 2.30–2.92 (5H, m), 2.48 (2H, t, J=7 Hz), 3.52 (4H, s), 3.90 (3H, broad s), 6.65–7.50 (4H, m), 7.28 (10H, s).

(b) 1-(2-Methylphenoxy)-3-(1-methyl-3-aminopropylamino)-2-propanol.

NMR(CDCl$_3$) δ: 1.09 (3H, d, J=6 Hz), 1.54 (2H, q, J=6 Hz), 2.21 (3H, s), 2.30–3.03 (5H, m), 3.30 (4H, s), 3.98 (3H, broad s), 6.62–7.38 (4H, m).

(c) 1-(2-Methylphenoxy)-3-[1-methyl-3-(3-chloro-6-pyridazinylamino)propylamino]-2-propanol.

NMR(CDCl$_3$) δ: 1.15 (3H, d, J=6 Hz), 1.74 (2H, q, J=6 Hz), 2.20 (3H, s), 2.60–3.30 (6H, m), 3.49 (2H, t, J=6 Hz), 4.01 (3H, broad s), 6.59 (1H, d, J=9 Hz), 6.63–7.38 (4H, m), 7.05 (1H, d, J=9 Hz).

(d) 1-(2-Methylphenoxy)-3-[1-methyl-3-(3-ethoxycarbonylhydrazino-6-pyridazinylamino)propylamino]-2-propanol.

Melting point: 115.4°–118.8° C.

NMR(CDCl$_3$) δ: 1.13 (3H, d, J=6 Hz), 1.24 (3H, t, J=7 Hz), 1.68 (2H, q, J=7 Hz), 2.23 (3H, s), 2.62–3.07 (3H, m), 3.38 (2H, t, J=7 Hz), 3.70–6.00 (5H, m), 4.02 (3H, broad s), 4.16 (2H, q, J=7 Hz), 6.55 (1H, d, J=9.5 Hz), 6.58–7.40 (4H, m), 6.95 (1H, d, J=9.5 Hz).

(e) 1-(2-Methylphenoxy)-3-[1-methyl-3-(3-hydrazino-6-pyridazinylamino)propylamino]-2-propanol hydrochloride.

Melting point: 169.0°–171.6° C.

NMR(D$_2$O) δ: 1.45 (3H, d, J=6 Hz), 1.98–2.45 (2H, m), 2.23 (3H, s), 3.17–3.85 (5H, m), 4.00–4.60 (3H, m), 6.73–7.40 (4H, m), 7.47 (2H, s).

Some examples for the preparation of drugs containing the compounds of this invention are shown below.

EXAMPLE A

Tablets:

Tablets containing 5 mg or 20 mg, per tablet, of the active compound of this invention were prepared in accordance with the following recipes.

| Ingredients | mg/tablet |
|---|---|
| Recipe 1-a (5 mg tablets) | |
| 1-(2-Chloro-3-methylphenoxy)-3-[1,1-dimethyl-2-(3-hydrazino-6-pyridazinyloxy)ethylamino]-2-propanol hydrochloride | 5 |
| Lactose | 137.2 |
| Starch | 44.8 |
| Carboxymethylcellulose calcium | 10 |
| Talc | 2 |
| Magnesium stearate | 1 |
| | 200.0 mg |
| Recipe 1-b (20 mg tablets) | |
| 1-(2-Chloro-3-methylphenoxy)-3-[1,1-dimethyl-2-(3-hydrazino-6-pyridazinyloxy)ethylamino]-2-propanol hydrochloride | 20 |
| Lactose | 122.2 |
| Starch | 44.8 |
| Carboxymethylcellulose calcium | 10 |
| Talc | 2 |
| Magnesium stearate | 1 |
| | 200.0 mg |

Specifically, crystals of the 1-(2-chloro-3-methylphenoxy)-3-[1,1-dimethyl-2-(3-hydrazino-6-pyridazinyloxy)-ethylamino]-2-propanol hydrochloride were pulverized, and well mixed with lactose and starch. A 10% starch paste was added to the mixture and they were mixed with stirring to prepare granules. After drying, the granules were adjusted to a particle diameter of about 840 microns and mixed with talc and magnesium stearate. The mixture was tableted.

EXAMPLE B

Capsules:

| Recipe 2 (20 mg capsule) | |
|---|---|
| Ingredients | mg/capsule |
| 1-(2-Chloro-3-methylphenoxy)-3-[1,1-dimethyl-2-(3-hydrazino-6-pyridazinyloxy)ethylamino]-2-propanol hydrochloride | 20 |
| Lactose | 57.8 |
| Starch | 30 |
| Magnesium stearate | 2.2 |
| | 110.0 mg |

Crystals of the 1-(2-chloro-3-methylphenoxy)-3-[1,1-dimethyl-2-(3-hydrazino-6-pyridazinyloxy)ethylamino]-2-propanol hydrochloride were well pulverized and mixed with starch, lactose and magnesium stearate. After good mixing, the mixture was filled in No. 5 capsules.

What we claim is:

1. A hydrazinopyridazine compound represented by the formula:

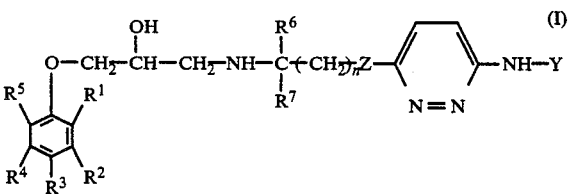

wherein

R$^1$ represents a hydrogen atom; a halogen atom; a cyano group; a C$_1$–C$_5$ alkyl group which may optionally be substituted by a halogen atom, a C$_1$–C$_5$ alkoxy or tetrahydrofurfuryloxy group; a C$_1$–C$_5$ alkoxy group which may optionally be substituted by a C$_1$–C$_5$ alkoxy group; an allyl group; an allyloxy group; or an ethynyl group;

R$^2$ represents a hydrogen, a halogen atom, a C$_1$–C$_5$ alkyl group, a C$_1$–C$_5$ alkoxy group, or an allyl group, R$^3$, R$^4$, and R$^5$, independently from each other, represent a hydrogen atom, a halogen atom, or a C$_1$–C$_5$ alkyl group which may optionally be substituted by a C$_1$–C$_5$ alkoxy group, R$^6$ and R$^7$, both represent a methyl group, Y represents —NH$_2$, —NH—COOC$_2$H$_5$, or

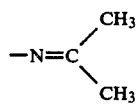

Z represents —O—, —S—, or

in which R$^8$ represents a hydrogen atom or a C$_1$–C$_5$ alkyl group, and n is 1 or 2 or its salt with the proviso that at least three of R$_1$, R$_2$, R$_3$, R$_4$ and R$_5$ are hydrogen atoms, said alkyl groups are straight chain alkyl groups and the alkyl groups in said alkoxy groups are straight chain alkyl groups.

2. The compound of claim 1 wherein Z represents —O—.

3. The compound of claim 1 wherein R$^1$ represents a chlorine atom or a methyl, trifluoromethyl or ethynyl group.

4. The compound of claim 1 which is 1-(2-chlorophenoxy)-3-[1,1-dimethyl-2-(3-hydrazino-6-pyridazinyloxy)-ethylamino]-2-propanol, 1-(2-methylphenoxy)-3-[1,1-dimethyl-2-(3-hydrazino-6-pyridazinyloxy)ethylamino]-2-propanol, 1-(2-trifluoromethylphenoxy)-3-[1,1-dimethyl-2-(3-hydrazino-6-pyridazinyloxy)ethylamino]-2-propanol, or 1-(2-ethynylphenoxy)-3-[1,1-dimethyl-2-(3-hydrazino-6-pyridazinyloxy)ethylamino]-2-propanol.

5. A pharmaceutical composition comprising a hydrazino-pyridazine compound of the formula

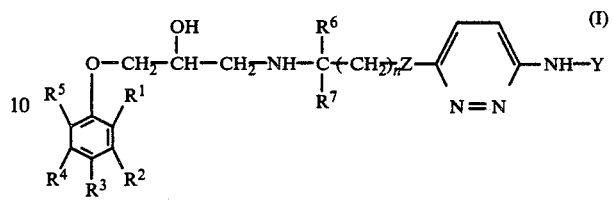

wherein R$^1$, R$^2$, R$^3$, R$^5$, R$^6$, Y, Z and n are as defined in claim 1, or its pharmaceutically acceptable salt, and a pharmaceutically acceptable carrier or diluent.

6. A method for the treatment of hypertension which comprises administering an anti-hypertensive amount of the compound the formula (I) as defined in claim 1 or a pharmaceutically acceptable salt thereof, to a patient suffering from hypertension.

7. The compound of claim 1 wherein n is 1.

8. The compound according to claim 2 wherein n is 1.

9. The compound of claim 3 wherein n is 1.

10. The compound of claim 4 which is 1-(2-chlorophenoxy)-3-[1,1-dimethyl-2-(3-hydrazino-6-pyridazinyloxy)ethylamino]-2-propanol.

11. The compound according to claim 4 which is 1-(2-methylphenoxy)-3-[1,1-dimethyl-2-(3-hydrazino-6-pyridazinyloxy)ethylamino]-2-propanol.

* * * * *